United States Patent
Almansa et al.

(10) Patent No.: US 6,838,476 B1
(45) Date of Patent: Jan. 4, 2005

(54) IMIDAZOLES WITH ANTI-INFLAMMATORY ACTIVITY

(75) Inventors: Carmen Almansa, Barcelona (ES); Concepción Gonzalez, Sant Boi de LLobregat (ES); Ma Carmen Torres, Badalona (ES)

(73) Assignee: J. Uriach & Cia, SA, Barcelona (ES)

( * ) Notice: Subject to any disclaimer, the term of this patent is extended or adjusted under 35 U.S.C. 154(b) by 0 days.

(21) Appl. No.: 09/807,458
(22) PCT Filed: Oct. 15, 1999
(86) PCT No.: PCT/ES99/00327
 § 371 (c)(1),
 (2), (4) Date: Jul. 5, 2001
(87) PCT Pub. No.: WO00/23426
 PCT Pub. Date: Apr. 27, 2000

(30) Foreign Application Priority Data

Oct. 16, 1998 (ES) .............................................. 9802222

(51) Int. Cl.⁷ .................. A61K 31/4164; C07D 233/64
(52) U.S. Cl. .................. 514/399; 548/333.5; 548/343.1
(58) Field of Search ...................... 514/399; 548/343.1, 548/333.5

(56) References Cited

U.S. PATENT DOCUMENTS

| | | | | |
|---|---|---|---|---|
| 4,576,958 A | * | 3/1986 | Wexler et al. | 514/400 |
| 5,620,999 A | * | 4/1997 | Weirer et al. | 514/398 |
| 5,932,598 A | * | 8/1999 | Talley et al. | 514/341 |

FOREIGN PATENT DOCUMENTS

WO  WO 9603387  * 2/1996

* cited by examiner

Primary Examiner—Joseph K. McKane
Assistant Examiner—Kamal Saeed
(74) Attorney, Agent, or Firm—Rothwell, Figg, Ernst & Manbeck

(57) ABSTRACT

Compounds of formula I wherein: one of X or Y represents N and the other represents C; $R_1$ represents hydrogen, methyl, halogen, cyano, nitro, —CHO, —COCH$_3$ or —COOR$_4$; P$R_2$ represents optionally-substituted aryl or heteroaryl; $R_3$ represents $C_{1-8}$ alkyl, $C_{1-8}$ haloalkyl or —NR$_4$R$_6$; $R_4$ represents hydrogen, $C_{1-8}$ alkyl or arylC$_{0-8}$ alkyl; $R_6$ represents hydrogen, $C_{1-8}$ alkyl, arylC$_{1-8}$ alkyl, —COR$_8$ or —COOR$_8$; $R_8$ represents $C_{1-8}$ alkyl or $C_{1-8}$ haloalkyl; aryl in the above definitions represents phenyl or naphthyl; and heteroaryl in the above definitions represents pyridine, pyrazine, pyrimidine or pyridazine, which can be optionally fused to a benzene ring. These compounds are useful as cyclooxygenase-2 inhibitors.

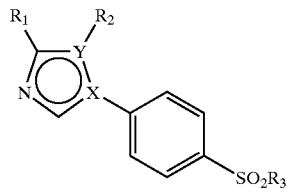

26 Claims, No Drawings

IMIDAZOLES WITH ANTI-INFLAMMATORY ACTIVITY

FIELD OF THE INVENTION

The present invention relates to a new series of imidazoles with anti-inflammatory activity, as well as to a process for their preparation, to the pharmaceutical compositions that contain these compounds and to their use in medicine.

BACKGROUND OF THE INVENTION

In many acute as well as chronic inflammatory processes, substances derived from the metabolism of arachidonic acid are involved. These form a large family of compounds of lipidic nature that are the result of the action of a series of enzymes which form what is called the arachidonic acid cascade. The most important one from the therapeutic point of view is prostaglandin G/H synthase (PGHS), also known as cyclooxygenase (COX), which catalyzes the formation of vasoactive and inflammatory substances such as prostaglandins ($PGE_2$, $PGD_2$, $PGF_2$), prostacyclin ($PGI_2$) and thromboxane $A_2$ ($TXA_2$).

Inhibition of cyclooxygenase (COX) is the mechanism of action responsible for the effect of most anti-inflammatory drugs that are on the market (non-steroidal anti-inflammatory drugs, NSAIDs). Said inhibition also reduces the levels of prostaglandins at gastric level, which, taking into account the protective role of said molecules on the gastric mucosa, has been correlated to the well known gastric effects of NSAIDs.

At the beginning of the 90's two cyclooxygenase isoforms, COX-1 and COX-2, were described. COX-1 is the constitutive isoform, present in many tissues, but preferentially in the stomach, kidney and platelets. Its inhibition is responsible for the gastric and renal effects of NSAIDs. On the other hand, COX-2 is an inducible isoform, which is expressed as a consequence of an inflammatory or mitogenic stimulus in a wide range of tissues such as macrophages, chondrocytes, fibroblasts and endothelial cells.

The discovery of the inducible isoenzyme of PGHS ($PGHS_2$ or COX-2) has allowed the synthesis of selective COX-2 inhibitors which presumably improve the gastric tolerance of these drugs, since as they inhibit the constitutive form present in the stomach to a lesser extent, they exhibit reduced ulcerogenic potency (one of the most characteristic side effects of non-selective inhibitors). The present invention describes new cyclooxygenase inhibitors with selectivity for the isoform 2 (COX-2).

DESCRIPTION OF THE INVENTION

The present invention relates to the new compounds of general formula I:

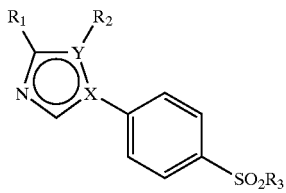

wherein:
one of X or Y represents N and the other represents C;
$R_1$ represents hydrogen, methyl, halogen, cyano, nitro, —CHO, —$COCH_3$ or —$COOR_4$;

$R_2$ represents aryl or heteroaryl optionally substituted with one or more groups independently selected from halogen, $C_{1-8}$ alkyl, $C_{1-8}$ haloalkyl, $R_4OC_{0-8}$ alkyl, $R_4SC_{0-8}$ alkyl, cyano, nitro, —$NR_4R_6$, —$NR_4SO_2R_5$, —$SOR_5$, —$SO_2R_5$, —$SO_2NR_4R_6$, or —$CONR_4R_6$;

$R_3$ represents $C_{1-8}$ alkyl, $C_{1-8}$ haloalkyl or —$NR_4R_6$;

$R_4$ represents hydrogen, $C_{1-8}$ alkyl, or aryl$C_{0-8}$ alkyl (where the aryl group can be optionally substituted with one or more groups selected from $C_{1-8}$ alkyl, halogen, $C_{1-8}$ haloalkyl, cyano, nitro, $R_7OC_{0-8}$ alkyl, $R_7SC_{0-8}$ alkyl, —$NR_7R_8$, —$NR_7COR_5$, —$COR_7$ or —$COOR_7$);

$R_5$ represents $C_{1-8}$ alkyl or $C_{1-8}$ haloalkyl;

$R_6$ represents hydrogen, $C_{1-8}$ alkyl, aryl$C_{1-8}$ alkyl (where the aryl group can be optionally substituted with one or more groups selected from $C_{1-8}$ alkyl, halogen, $C_{1-8}$ haloalkyl, cyano, nitro, $R_7OC_{0-8}$ alkyl, $R_7SC_{0-8}$ alkyl, —$NR_7R_8$, —$NR_7COR_5$, —$COR_7$ or —$COOR_7$), —$COR_8$ or —$COOR_8$;

$R_7$ represents hydrogen, $C_{1-8}$ alkyl or benzyl;

$R_8$ represents $C_{1-8}$ alkyl or $C_{1-8}$ haloalkyl;

aryl in the above definitions represents phenyl or naphthyl; and heteroaryl in the above definitions represents pyridine, pyrazine, pyrimidine or pyrdazine, which can be optionally fused to a benzene ring.

The present invention also relates to the addition salts of the compounds of the invention as well as to their solvates and prodrugs. The term prodrug refers to any precursor of a compound of formula I which can be broken down and release the compound of formula I in vivo.

Some compounds of formula I can have chiral centers, which can give rise to various stereoisomers. The present invention relates to each one of the individual stereoisomers as well as to their mixtures. Moreover, some of the compounds of the present invention can show cis/trans isornery. The present invention relates to each one of the geometric isomers as well as to their mixtures.

The present invention also relates to the pharmaceutical compositions which comprise an effective amount of a compound of formula I or a pharmaceutically acceptable salt, solvate or prodrug thereof in admixture with one or more pharmaceutically acceptable excipients.

The present invention also relates to the use of a compound of formula I or a pharmaceutically acceptable salt, solvate or prodrug thereof for the manufacture of a medicament for the treatment or prevention of diseases mediated by cyclooxygenase, specially cyclooxygenase-2.

The present invention also relates to the use of a compound of formula I or a pharmaceutically acceptable salt, solvate or prodrug thereof for the manufacture of a medicament for the treatment of inflammation, pain and/or fever.

The present invention also relates to the use of a compound of formula I or a pharmaceutically acceptable salt, solvate or prodrug thereof for the manufacture of a medicament for inhibiting prostanoid-induced smooth muscle contraction.

The present invention also relates to the use of a compound of formula I or a pharmaceutically acceptable salt, solvate or prodnrg thereof for the manufacture of a medicament for the treatment or prevention of dysmenorrhea, preterm labour, asthma and bronchitis.

The present invention also relates to the use of a compound of formula I or a pharmaceutically acceptable salt, solvate or prodrug thereof for the manufacture of a medicament for the treatment or prevention of cancer, preferably gastrointestinal cancers, and more preferably colon cancer.

The present invention also relates to the use of a compound of formula I or a pharmaceutically acceptable salt, solvate or prodrug thereof for the manufacture of a medicament for the treatment or prevention of cerebral infarction, epilepsy, and neurodegenerative diseases such as Alzheimer's disease and dementia.

The present invention also relates to the use of a compound of formula I or a pharmaceutically acceptable salt, solvate or prodrug thereof for the treatment or prevention of diseases mediated by cyclooxygenase, specially cyclooxygenase-2.

The present invention also relates to the use of a compound of formula I or a pharmaceutically acceptable salt, solvate or prodrug thereof for the treatment of inflammation, pain and/or fever.

The present invention also relates to the use of a compound of formula I or a pharmaceutically acceptable salt, solvate or prodrug thereof to inhibit prostanoid-induced smooth muscle contraction.

The present invention also relates to the use of a compound of formula I or a pharmaceutically acceptable salt, solvate or prodrug thereof for the treatment or prevention of dysmenorrhea, preterm labour, asthma and bronchitis.

The present invention also relates to the use of a compound of formula I or a pharmaceutically acceptable salt, solvate or prodrug thereof for the treatment or prevention of cancer, preferably gastrointestinal cancers, and more preferably colon cancer.

The present invention also relates to the use of a compound of formula I or a pharmaceutically acceptable salt, solvate or prodrug thereof for the treatment or prevention of cerebral infarction, epilepsy, and neurodegenerative diseases such as Alzheimer's disease and dementia.

The present invention also relates to a method of treating or preventing diseases mediated by cyclooxygenase, specially cyclooxygenase-2, in a mammal in need thereof, specially a human being, which comprises administering to said mammal a therapeutically effective amount of a compound of formula I or a pharmaceutically acceptable salt, solvate or prodrug thereof.

The present invention also relates to a method of treating inflammation, pain and/or fever in a mammal in need thereof, specially a human being, which comprises administering to said mammal a therapeutically effective amount of a compound of formula I or a pharmaceutically acceptable salt, solvate or prodrug thereof.

The present invention also relates to a method for inhibiting prostanoid-induced smooth muscle contraction in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing dysmenorrhea, preterm labour, asthma and bronchitis in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing cancer, preferably gastrointestinal cancers, and more preferably colon cancer in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing cerebral infarction, epilepsy, and neurodegenerative diseases such as Alzheimer's disease and dementia in a mammal in need thereof, specially a human being, which comprises administering to said mammal a therapeutically effective amount of a compound of formula I or a pharmaceutically acceptable salt, solvate or prodrug thereof.

Another object of the present invention is to provide a process for preparing the compounds of formula I, which comprises:

(a) when in a compound of formula I $R_1$ represents hydrogen or methyl, reacting an imine of formula II

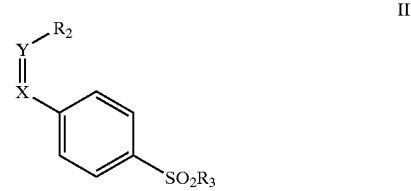

wherein X, Y, $R_2$ and $R_3$ have the meaning described above, with an isocyanide of formula III

wherein $R_1$ represents hydrogen or methyl and L represents a good leaving group; or (b) when in a compound of formula I $R_3$ represents $C_{1-8}$ alkyl or $C_{1-8}$ haloalkyl, oxidizing a thioether of formula VIII,

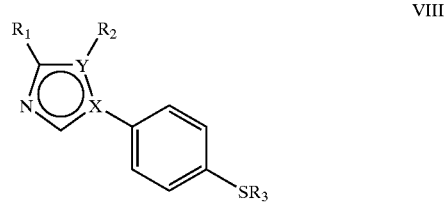

wherein $R_3$ represents $C_{1-8}$ alkyl or $C_{1-8}$ haloalkyl and X, Y, $R_1$ and $R_2$ have the meaning described above, with a suitable oxidizing agent; or (c) when in a compound of formula I $R_3$ represents —$NH_2$, reacting a compound of formula IX

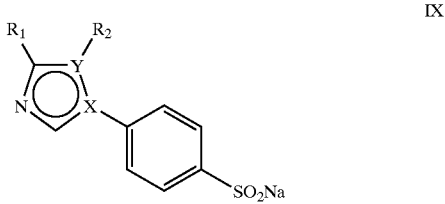

wherein X, Y, $R_1$ and $R_2$ have the meaning described above, with hydroxylamine-O-sulfonic acid; or (d) when in a compound of formula I $R_3$ represents —$NR_4R_6$, reacting a compound of formula XI

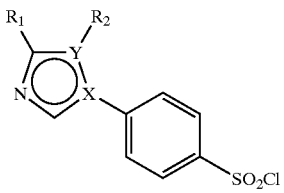

XI wherein X, Y, $R_1$ and $R_2$ have the meaning described above, with an amine of formula $HNR_4R_6$; or (e) when in a compound of formula I $R_1$ represents halogen and X represents N, reacting a compound of formula I wherein $R_1$ represents hydrogen with a suitable halogenating agent;

(f) when in a compound of formula I $R_1$ represents halogen and Y represents N, reacting a compound of formula I wherein $R_1$ represents hydrogen with a strong base and a suitable halogenating agent;

(g) converting, in one or a plurality of steps, a compound of formula I into another compound of formula I; and (h) if desired, after the above steps, reacting a compound of formula I with an acid to give the corresponding addition salt.

In the above definitions, the term $C_{1-8}$ alkyl, as a group or a part of a group, means a lineal or branched alkyl group containing from 1 to 8 carbon atoms. Examples include among others methyl, ethyl, propyl, isopropyl, butyl, isobutyl, sec-butyl, tert-butyl, pentyl, isopentyl, neopentyl, hexyl, heptyl and octyl. A $C_{0-8}$ alkyl group means that additionally the alkyl group can be absent (that is, that a covalent bond is present).

A halogen radical or its abbreviation halo means fluoro, chloro, bromo or iodo.

A $C_{1-8}$ haloalkyl group means a group resulting from the substitution of one or more hydrogen atoms of a $C_{1-8}$ alkyl group with one or more halogen atoms (that is, fluoro, chloro, bromo or iodo), which can be the same or different. Examples include trifluoromethyl, fluoromethyl, 1-chloroethyl, 2-chloroethyl, 1-fluoroethyl, 2-fluoroethyl, 2-bromoethyl, 2-iodoethyl, pentafluoroethyl, 3-fluoropropyl, 3-chloropropyl, 2,2,3,3-tetrafluoropropyl, 2,2,3,3-pentafluoropropyl, heptafluoropropyl, 4-fluorobutyl, nonafluorobutyl, 5-fluoropentyl, 6-fluorohexyl, 7-fluoroheptyl and 8-fluorooctyl.

An aryl$C_{1-8}$ alkyl group means a group resulting from the substitution of a hydrogen atom of a $C_{1-8}$ alkyl group with an aryl group like those defined above, that is phenyl or naphthyl, which can be optionally substituted as described above. Examples include among others benzyl, 1-phenylethyl, 2-phenylethyl, 3-phenylpropyl, 2-phenylpropyl, 1-phenylpropyl, 4-phenylbutyl, 3-phenylbutyl, 2-phenylbutyl, 1-phenylbutyl, 5-phenylpentyl, 6-phenylhexyl, 7-phenylheptyl and 8-phenyloctyl, wherein the phenyl group can be optionally substituted. An aryl$C_{0-8}$ alkyl group means that additionally includes an aryl group when the alkyl group is absent (that is, when it is $C_0$ alkyl).

In the definition of $R_2$ the term aryl means phenyl or naphthyl. The term heteroaryl in the definition of $R_2$ means a pyridine, pyrazine, pyrimidine or pyridazine ring, which can be optionally fused to a benzene ring, thus giving rise to a quinoline, isoquinoline, quinoxaline, quinazoline, phthalazine, or cinnoline ring. The heteroaryl group can be linked to the rest of the molecule of formula I through any carbon atom in any of the rings (in case it contains a fused benzene ring).

As it has already been mentioned above, the aryl or heteroaryl group represented by $R_2$ can be optionally substituted with one or more, preferably from one to three, groups independently selected from halogen, $C_{1-8}$ alkyl, $C_{1-8}$ haloalkyl, $R_4OC_{0-8}$ alkyl, $R_4SC_{0-8}$ alkyl, cyano, nitro, —$NR_4R_6$, —$NR_4SO_2R_5$, —$SOR_5$, —$SO_2R_5$, —$SO_2NR_4R_6$ or —$CONR_4R_6$. The substituent(s), when there are more than one, can be in any available position of the aryl or heteroaryl group.

Although the present invention includes all the compounds above mentioned, those compounds of formula I are preferred wherein, independently or in any compatible combination:

$R_1$ represents halogen, more preferably chloro; and/or $R_2$ represents phenyl or pyridine optionally substituted with one or more groups independently selected from halogen, $C_{1-8}$ alkyl, $C_{1-8}$ haloalkyl, $R_4OC_{0-8}$ alkyl, $R_4SC_{0-8}$ alkyl, cyano, nitro, —$NR_4R_6$, —$NR_4SO_2R_5$, —$SOR_5$, —$S_2R_5$, —$SO_2NR_4R_6$, or —$CONR_4R_6$; and/or $R_3$ represents methyl or —$NH_2$; and/or X represents N.

Thus, a preferred class of compounds of the present invention are those compounds of formula I wherein $R_3$ represents methyl or —$NH_2$.

A more preferred class of compounds of the present invention are those compounds of formula I wherein $R_3$ represents methyl or —$NH_2$, and $R_1$ represents halogen.

A still more preferred class of compounds of the present invention are those compounds of formula I wherein $R_3$ represents methyl or —$NH_2$, and $R_1$ represents chloro.

A particularly preferred class of compounds of the present invention are those compounds of formula I wherein $R_3$ represents methyl or —$NH_2$, $R_1$ represents chloro and X represents N.

Another particularly preferred class of compounds of the present invention are those compounds of formula I wherein $R_3$ represents methyl or —$NH_2$, $R_1$ represents chloro, X represents N, and $R_2$ represents phenyl or pyridine optionally substituted with one or more groups independently selected from halogen, $C_{1-8}$ alkyl, $C_{1-8}$ haloalkyl, $R_4OC_{0-8}$ alkyl, $R_4SC_{0-8}$ alkyl, cyano, nitro, —$NR_4R_6$, —$NR_4SO_2R_5$, —$SOR_5$, —$SO_2R_5$, —$SO_2NR_4R_6$, or —$CONR_4R_6$.

The compounds of the present invention contain one or more basic nitrogens and, consequently, they can form salts with organic and inorganic acids, which are also included in the present invention. There is no limitation on the nature of said salts, provided that, when used for therapeutic purposes, they are pharmaceutically acceptable. Examples of said salts include salts with inorganic acids such as hydrochloric acid, hydrobromic acid, hydroiodic acid, nitric acid, perchloric acid, sulfuric acid or phosphoric acid; and salts with organic acids, such as methanesuffonic acid, trifluoromethanesulfonic acid, ethanesulfonic acid, benzenesulfonic acid, p-toluenesulfonic acid, fumaric acid, oxalic acid, acetic acid or maleic acid, among others. The salts can be prepared by treatment of a compound of formula I with a sufficient amount of the desired acid to give the salt in a conventional manner. The compounds of formula I and their salts differ in certain physical properties, such as solubility, but they are equivalent for the purposes of the invention.

Some compounds of the present invention can exist in solvated form, including hydrated forms. In general, the solvated forms, with pharmaceutically acceptable solvents such as water, ethanol and the like, are equivalent to the unsolvated form for the purposes of the invention.

Some compounds of the present invention can exist as various diastereoisomers and/or various optical isomers. Diastereoisomers can be separated by conventional techniques such as chromatography or fractional crystallization. The optical isomers can be resolved using conventional techniques of optical resolution, to give the optically pure isomers. This resolution can be performed upon any synthetic intermediate is chiral or upon the products of general formula I. The optically pure isomers can also be individually obtained using enantiospecific synthesis. The present invention covers both the individual isomers and the mixtures (for example racemic mixtures), whether obtained by synthesis or by physically mixing them up.

Furthermore, some of the compounds of the present invention can exhibit cis/trans isomery. The present invention includes each one of the geometric isomers as well as the mixtures thereof.

It is also an object of the present invention to provide a process for preparing the compounds of formula I. As will be obvious to a person skilled in the art, the precise method used for the preparation of a given compound can vary depending on its chemical structure. Furthermore, in most processes that are detailed below it may be necessary or appropriate to protect the labile or reactive groups using conventional protecting groups. Both the nature of said protecting groups and the processes for their introduction and removal are well known and belong to the state of the art (see for example Greene T. W., "Protective Groups in Organic Synthesis", Oohn Wiley & Sons, New York, 1981).

The compounds of formula I wherein $R_1$ represents hydrogen or methyl are in general obtained by reacting an imine of formula II with an isocyanide of formula III, as shown in the following scheme:

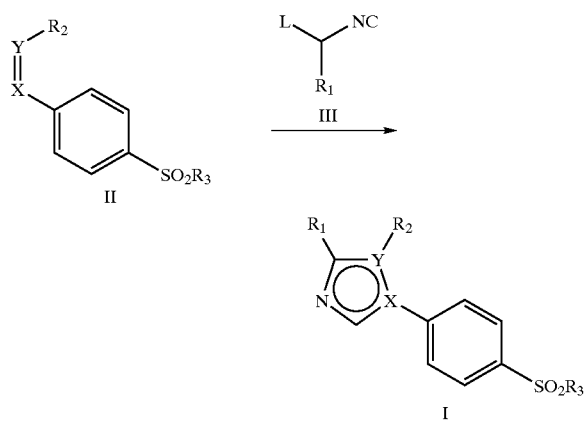

wherein $R_1$ represents hydrogen or methyl, X, Y, $R_2$ and $R_3$ have the meaning described above, and L represents a good leaving group such as tosyl or 1H-benzotriazol-1yl.

This reaction is carried out in the presence of a base such as $K_2CO_3$ in a suitable solvent such as methanol-dimethoxyethane mixtures, and heating, preferably at reflux.

The imines of formula II can be prepared by condensation of an aldehyde of formula $R_2$—CHO (IV) with an amine of formula $R_3SO_2$—$C_6H_4$—$NH_2$ (V) when X is N or by condensation of an aldehyde of formula $R_3SO_2$—$C_6H_4$—CHO (VI) with an amine of formula $R_2$—$NH_2$ (VII) when Y is N, heating at reflux in a suitable solvent such as benzene or toluene in a Dean Stark.

The isocyanides of formula III are commercially available such as tosylmethylisocyanide and 1H-benzotriazol-1-ylmethylisocyanide or can be prepared by alkylation of these with methyl iodide using the method described in the literature (A. M. van Leusen at al., *Tetrahedron Lett* 1975, 3487–88).

A compound of formula I wherein $R_3$ represents $C_{1-8}$ alkyl or $C_{1-8}$ haloalkyl can also be prepared from the corresponding thioether of formula VIII

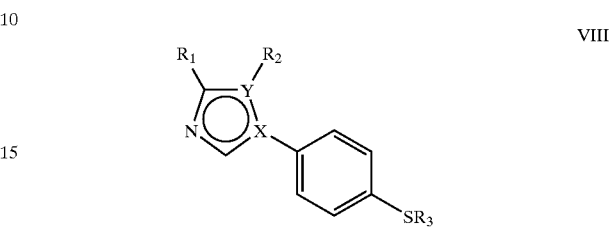

wherein $R_3$ represents $C_{1-8}$ alkyl or $C_{1-8}$ haloalkyl and X, Y, $R_1$ and $R_2$ have the meaning described above, by oxidation with a suitable oxidizing agent such as m-chloroperbenzoic acid, magnesium monoperoxyphthalate or Oxone® in a suitable solvent such as a halogenated hydrocarbon, for example dichloromethane.

A compound of formula I wherein $R_3$ represents —$NH_2$ can also be prepared from the corresponding sodium sulfinate of formula IX,

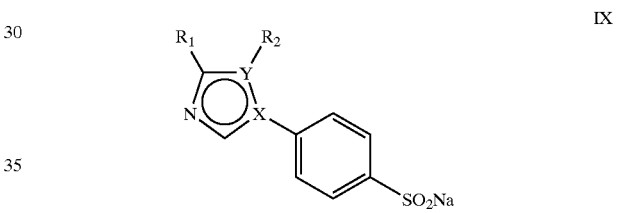

wherein X, Y, $R_1$ and $R_2$ have the meaning described above, by reaction with hydroxylamine-O-sulfonic acid in a suitable solvent such as water or water-tetrahydrofuran mixtures.

The compounds of formula IX are prepared from the corresponding methylsulfoxide X, that is a compound analogous to IX but with a —$SOCH_3$ group instead of —$SO_2Na$, by a process that involves treatment with acetic anhydride to give the corresponding acetoxymethylthio derivative (—$SCH_2OAc$), which is oxidized with a suitable oxidizing agent such as magnesium monoperoxyphthalate to give the derivative —$SO_2CH_2OAc$, which is converted into a sodium sulfinate of formula IX by treatment with a base, for example sodium hydroxide.

A compound of formula I wherein $R_3$ represents —$NR_4R_6$ can also be prepared from a chlorosulfonyl derivative of formula XI

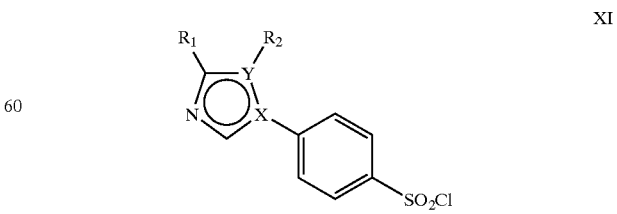

wherein X, Y, $R_1$ and $R_2$ have the meaning described above, by reaction with an amine of formula $HNR_4R_6$ (XII). The compounds of formula XI can be prepared from a sodium sulfinate of formula IX by chlorination with thionyl chloride. Alternatively, a compound of formula XI can be prepared from a compound of formula XIII

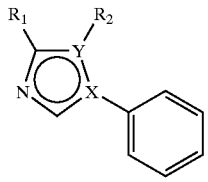

XIII wherein X, Y, $R_1$ and $R_2$ have the meaning described above, by treatment with a halosulfonic acid, for example chlorosulfonic acid.

The compounds VIII, X and XIII can be prepared following the same general method described above for preparing compounds of formula I but starting from compounds II which contain a —$SR_3$, —$SOCH_3$ or —H group, respectively, instead of —$SO_2R_3$. The derivatives X can also be prepared from a compound of formula VIII wherein $R_3$=$CH_3$ by oxidation with a suitable oxidizing agent.

Some compounds of formula I can also be obtained by interconversion from another compound of formula I, in one or a plurality of steps, using standard reactions in organic chemistry.

Thus, for example, a substituent $R_1$ can be transformed into another $R_1$ group, thus generating new compounds of formula I.

Many of the compounds of formula I wherein $R_1$ is different from hydrogen can be prepared from the corresponding compound I wherein $R_1$ represents hydrogen by conventional reactions, widely used in organic chemistry. The compounds of formula I wherein $R_1$ is halogen can be prepared from the corresponding compound I wherein $R_1$ represents hydrogen by treatment with a suitable halogenating agent such as an N-halosuccinimide or $Br_2$ when X=N, and by treatment with a strong base such as butyllithium to generate an anion and subsequent reaction with a suitable halogenating agent such as an N-halosuccinimide when Y=N. Other examples of transformations include: the treatment of a compound of formula I wherein Y=N with a strong base such as butyllithium to generate an anion preferentially at position 2 of the imidazole, and subsequent reaction with an electrophilic reagent such as a suitable alkylating agent, for example methyl iodide, a suitable acylating agent (to give a compound I wherein $R_1$=—$COCH_3$), tosylcyanide (to give a compound I wherein $R_1$=cyano) or dimethylformamide (to give a compound I wherein $R_1$=CHO); the acylation by treatment with an acetyl chloride in the presence of a base such as triethylamine to give a compound I wherein $R_1$=—$COCH_3$: the nitration by treatment with a suitable nitration reagent such as $HNO_3$/$H_2SO_4$; the transformation into a —CHO or —$COOR_4$ group by treatment with formaldehyde to give the hydroxymethyl derivative (—$CH_2OH$) and subsequent oxidation thereof to give an aldehyde or an ester.

Other transformations between substituents $R_1$ include: the transformation of a halogen into a variety of substituents by treatment with a base such as butyllithium to give an anion which will react with suitable electrophilic reagents such as those above described; the transformation of a halogen atom, for example chloro, into a hydrogen atom by hydrogenation in the presence of a catalyst such as Pd/C in a suitable solvent such as an alcohol; the hydrolysis of an ester group under the usual conditions, for example by treatment with a base, to give a carboxy group, which can be removed by decarboxylation by treatment with an acid such as $H_2SO_4$ at reflux; the transformation of a —CHO group into a cyano group by treatment with hydroxylamine-O-sulfonic acid at reflux.

Likewise, new compounds of formula I can be prepared by transformations between the substituents of the group $R_2$. As examples of these transformations we can mention the following: the reduction of a nitro group to give an amino group, for example by hydrogenation in the presence of a suitable catalyst such as Pd/C or by treatment with a suitable reducing agent such as $SnCl_2$; the reaction of an amino group with a sulfonyl halide ($HalSO_2R_5$) to give the corresponding sulfonamide (—$NR_4SO_2R_5$); the acylation of an amino group by treatment with a suitable acylating reagent such as an acid halide or an anhydride; the alkylation of an amino group by treatment for example with a suitable alkylating agent; the reductive amination of an amino group with a ketone to give an alkyl- or dialkylamino group; the hydrogenolysis of a mono- or di-benzylamine by hydrogenation in the presence of a suitable catalyst such as Pd/C, to give the corresponding amine; the transformation of a hydrogen atom into a sulfonyl halide, for example sulfonyl chloride (—$SO_2Cl$), by treatment with a halosulfonic acid, for example chlorosulfonic acid, and subsequent reaction of the resulting halosulfonyl group with an amine ($NHR_4R_6$) to give the corresponding sulfonamide (—$SO_2NR_4R_6$); the transformation of an amino group into a sulfonyl halide (—$SO_2Hal$), by treatment with $SO_2$ in the presence of $CuCl_2$, which is transformed into a sulfonamide (—$SO_2NR_4R_6$) by treatment with the corresponding amine $NHR_4R_6$; the oxidation of a thioether group with a suitable oxidizing agent to give a —$SOR_5$ or —$SO_2R_5$ group.

This type of reactions are widely described in the literature and are carried out under the standard conditions used in organic chemistry for this kind of transformations. Some of them are illustrated in the examples.

All these interconversion reactions between substituents can be performed upon the final compounds as well as upon any of their synthetic intermediates.

The aldehydes of formulae IV and VI and the amines of formulae V, VII and XII are commercially available, are widely described in the literature or can be prepared by methods analogous to those described starting from commercially available products. For example, an aldehyde of formula IV or VI can be prepared from the corresponding carboxylic acid in a sequence which comprises the transformation into an ester, for example an ethyl ester, under the usual conditions of ester formation, subsequent reduction of the ester to the alcohol with a suitable ester reducing agent such as lithium aluminum hydride, and finally oxidation of the alcohol to the aldehyde with a suitable oxidizing agent such as dimethylsulfoxide/oxalyl chloride.

The salts of the compounds of formula I can be prepared by conventional methods by treatment for example with an acid such as hydrochloric acid, sulfuric acid, nitric acid, oxalic acid or methanesulfonic acid.

As it has been mentioned above, the compounds of the present invention act by inhibiting the cyclooxygenase-2 enzyme (COX-2). Therefore, they are useful for the treatment or prevention of inflammation, pain and/or fever associated with a wide range of diseases or pathologies, which include among others: rheumatic fever; symptoms associated with influenza or other viral infections; common cold; low back and neck pain; dysmenorrhea; headache; toothache; myositis; neuralgia; synovitis; bursitis; arthritis, including rheumatoid arthritis and juvenile arthritis; degenerative joint diseases, including osteoarthritis; gout and ankylosing spondylitis; lupus erythematosus; tendinitis; sprains, strains and other similar injures, such as those occurred during sport performance; pain following surgical or dental procedures; and pain associated with cancer. They are also useful in the treatment of skin inflammatory diseases, including psoriasis, eczema, burns and dermatitis.

The compounds of the present invention can also be useful for the treatment of other pathologies mediated by COX-2. For example, the compounds of formula I can inhibit cell proliferation and consequently they can be useful for the treatment or prevention of cancer, specially of cancers that produce prostaglandins or that express cyclooxygenase. The compounds of the invention are useful for the treatment, for example, of liver, bladder, pancreas, ovary, prostate, cervix, lung, breast and skin cancer, and specially gastrointestinal cancers such as colon cancer.

The compounds of the present invention can also inhibit prostanoid-induced smooth muscle contraction and thus can be useful for the treatment of dysmenorrhea, preterm labour, asthma and bronchitis. Other uses of the compounds of formula I include the treatment or prevention of cerebral infarction, epilepsy, and neurodegenerative diseases, such as Alzheimer's disease and dementia.

Likewise, the compounds of the present invention can be used for treating inflammation in diseases such as vascular diseases, migraine, periarteritis nodosa, thyroiditis, aplastic anaemia, Hodgkin's disease, scleroderma, type I diabetes, myasthenia gravis, sarcoidosis, nephrotic syndrome, Behcet's syndrome, polymyositis, hypersensitivity, conjunctivitis, gingivitis and myocardial ischaemia.

Due to their selectivity for cyclooxygenase-2, the compounds of the present invention are useful as an alternative to non-steroidal anti-inflammatory drugs (NSAIDs), specially in those cases in which NSAIDs may be contraindicated.

According to the activity of the products herein described, the present invention also relates to compositions which contain a compound of the present invention, together with an excipient or other auxiliary agents if necessary. The compounds of the present invention can be administered in the form of any pharmaceutical formulation, the nature of which, as it is well known, will depend upon the route of administration and the nature of the pathology to be treated.

According to the present invention, solid compositions for oral administration include tablets, powders for extemporaneous suspensions, granulates and capsules. In tablets, the active component is admixed with at least one inert diluent such as lactose, starch, mannitol, microcrystalline cellulose or calcium phosphate; with a binding agent such as for example starch, gelatin, microcrystalline cellulose or polyvinylpyrrolidone; and with a lubricating agent, such as for example magnesium stearate, stearic acid or talc. Tablets can be coated by known techniques with the purpose of delaying their disintegration and absorption in the gastrointestinal tract, and thereby provide a sustained action over a longer period. Gastric or enteric coatings can be made with sugar, gelatin, hydroxypropylcellulose, acrylic resins, etc. Sustained-release tablets might also be obtained using an excipient which produces regressive osmosis, such as the galacturonic acid polymers. Preparations for oral use can also be presented as hard capsules of absorbable material, such as for example gelatin, wherein the active compound is mixed with an inert solid diluent and lubricating agents, or pasty materials, such as ethoxylated saturated glycerides, which might also provide controlled release. Soft gelatin capsules are also possible, wherein the active compound is mixed with water or an oily medium, for example coconut oil, liquid paraffin, or olive oil.

Powders and granulates for the preparation of suspensions by the addition of water can be obtained by mixing the active compound with dispersing or wetting agents; suspending agents, such as sodium carboxymethylcellulose, methylcellulose, hydroxypropylmethylcellulose, sodium alginate, polyvinylpyrrolidine, gum tragacanth, xantham gum, gum acacia, and one or more preservatives, such as methyl or propyl phydroxybenzoate. Other excipients can also be added, for example sweetening, flavouring and colouring agents.

Liquid forms for oral administration include emulsions, solutions, suspensions, syrups and elixirs containing commonly-used inert diluents, such as distilled water, ethanol, sorbitol, glycerol or propylene glycols. Said compositions can also contain coadjuvants such as wetting, suspending, sweetening, flavouring, preserving agents and buffers.

Injectable preparations, according to the present invention, for parenteral administration, comprise sterile aqueous or non-aqueous solutions, suspensions or emulsions, in a suitable non-toxic solvent or diluent. Examples of aqueous solvents or suspending media are distilled water for injection, Ringer's solution and isotonic sodium chloride solution. As non-aqueous solvents or suspending media propylene glycol, polyethylene glycol, vegetable oils such as olive oil, or alcohols such as ethanol can be used. These compositions can also contain coadjuvants, such as wetting, preserving, emulsifying and dispersing agents. They may be sterilized by any known method or prepared as sterile solid compositions which will be dissolved in water or any other sterile injectable medium immediately before use. It is also possible to start from sterile materials and keep them under these conditions throughout all the manufacturing process.

The dosage and frequency of doses will depend upon the nature and severity of the disease to be treated, the age and body weight of the patient, as well as the route of administration. In general, the daily dose for an adult will be comprised between 1 and 1000 mg per day, which can be administered as a single or divided doses. However, in special cases, doses outside these margins might be necessary. A person skilled in the art will be able to easily determine the suitable dose for each situation.

Some examples of representative formulations for tablets, capsules and injectable preparations are cited below. They can be prepared by conventional procedures and are useful for inhibiting cyclooxygenase-2.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |

-continued

| Injectable | |
|---|---|
| Compound of formula I | 100 mg |
| Benzylic alcohol | 0.05 mL |
| Propylene glycol | 1 mL |
| Water to | 5 mL |

The activity of the compounds of the present invention can be determined using the following tests:

Inhibition of cyclooxgenase-1 (COX-1) and cyclooxygenase-2 (COX-2) Activity in Human Blood Heparinized human blood from healthy volunteers who had not taken non-steroidal anti-inflammatory drugs (NSAIDs) for a week, and neither alcohol nor xanthines 24 h before blood collection, is used. Blood is divided into two groups; one will be used to determine COX-1 activity and the other one for COX-2. The procedure to follow will be different in each case.

For COX-1, 12-mL tubes are used. 5 μL of the test compound (in DMSO solution; in duplicate) are placed in each tube. Aditionally two tubes for blanks and two tubes for controls containing 5 μL of DMSO are used. Next, 1 mL of blood is added to each tube and they are stirred. The tubes are placed in a thermostatized bath at 37° C. for 5 h. Then, 5 μL of 5 mM ionophore A23187 is added to each tube, except to the blanks, and tubes are incubated for 30 min more at 37° C. After this time, the tubes are placed in ice and 100 μL of a 100 mM EGTA solution is added to stop the reaction. 2.5 mL of methanol is added to each tube to reach a final concentration of 70%. The tubes are stirred and frozen at −70° C. till their use. The COX-1 activity is determined by measuring thromboxane $B_2$ levels in the samples. Blood is defrozen and centrifuged at 2000 g for 10 min at 4° C. 1 mL of supematant is evaporated under nitrogen to dryness. The solid residue thus obtained is resuspended in 1 mL of saline and the thromboxane $B_2$ levels in these samples are determined using a kit (Kit Thromboxane $B_2$, Biotrak EIA system RPN220 Amershan), according to the manufacturer's instructions.

For COX-2, 3-mL tubes are prepared in duplicate containing 5 μL of the test compound (solution in DMSO) and 5 μL of vehicle in the case of blanks and controls. To each tube, 5 μL of a 2 mg/mL solution of aspirin in DMSO is also added (in order to inhibit COX-1 activity), and to all tubes except the blanks 5 μL of LPS is also added (in order to induce COX-2 activy). Finally, 1 mL of heparinized blood is added to each tube, and tubes are then stirred and placed in a thermostatized bath at 37° C. for 24 h. Then, tubes are centrifuged at 2000 g for 10 min at 4° C., the resulting plasma is collected and is frozen at −70° C. until use. COX-2 activity is determined by measuring prostaglandin $E_2$ levels in the samples. The plasma stored at −70° C. is defrozen and prostaglandin $E_2$ levels in these samples are determined using a kit (Kit Prostaglandin $E_2$, Biotrak EIA system RPN222 Amershan), according to the manufacturer's instructions.

The results obtained with representative compounds of the present invention are shown in the following table, where the % inhibition of COX-1 and COX-2 activities at a concentration of 10 or 1 μM of test compound is given, as indicated.

| Compound (no. example) | % inhibition | | |
|---|---|---|---|
| | COX-1 (10 μM) | COX-2 (10 μM) | COX-2 (1 μM) |
| 3 | 8.3 | 86.5 | — |
| 4 | 37.8 | 100 | 89 |
| 4(1) | 34 | 100 | — |
| 4(3) | 47.9 | 96 | 82.6 |
| 4(8) | 47.5 | 100 | 75.1 |
| 4(11) | 39.7 | 100 | 58.4 |
| 4(16) | 42.5 | 100 | — |
| 4(17) | 22.7 | 86.3 | 65 |
| 4(22) | 72.1 | 100 | 100 |
| 5 | 33.8 | 100 | 85.2 |
| 7 | 60.1 | 100 | 85.6 |
| 10 | 52.7 | 100 | 74.0 |
| 12 | 70.6 | 100 | 83.6 |
| 13(3) | 71.3 | 100 | 76.1 |
| 13(4) | — | 100 | — |

The results of the table above show that the compounds of formula I are potent and selective COX-2 inhibitors.

The following examples illustrate, but do not limit, the scope of the present invention. The following abbreviations have been used in the examples:

EtOAc: ethyl acetate
$Ac_2O$: acetic anhydride
NaOAc: sodium acetate
BuLi: butyllithium
DME: dimethoxyethane
DMSO: dimethylsulfoxide
EtOH: ethanol
$Et_2O$: diethyl ether
MeOH: methanol
$Et_3N$: triethylamine
THF: tetrahydrofuran

REFERENCE EXAMPLE 1

4-Methylsulfonylbenzaldehyde 5 g (33 mmol) of 4-methylthiobenzaldehyde was placed in a flask and was dissolved in 132 mL of $CH_2Cl_2$. The mixture was cooled to 0° C. and 20.61 g (66 mmol) of m-chloroperbenzoic acid was added. The mixture was stirred for 3 h at room temperature and was poured over $CHCl_3$, washed with saturated $NaHCO_3$ solution and dried over $MgSO_4$. The solvent was removed, yielding a crude product that was chromatographed on silica gel, using EtOAc-hexane mixtures of increasing polarity as eluent. The title compound of the example was obtained as a white solid (3.96 g, 65%).

M. p.: 157–159° C.; $^1$H-NMR (300 MHz, $CDCl_3$ δ TMS): 3.10 (s, 3 H), 8.09 (m, 4 H), 10.14 (s, 1 H).

REFERENCE EXAMPLE 2

4-Methylsulfonylaniline 67 mg of $Na_2WO_4$, 8 drops of acetic acid and 19 mL of $H_2O$ were placed in a flask and the mixture was heated to 65° C. 19 mL (153 mmol) of 4-methylthioaniline was added followed by 34.5 mL (337 mmol) of $H_2O_2$ dropwise. The mixture was stirred at 65° C. for 1.5 h and, after cooling, 800 mL of 1N HCl and 500 mL of $CHCl_3$ was added. The layers were separated and the aqueous phase was washed with more CHCl₃. The aqueous phase was basified with 25% NaOH and extracted with CHCl₃. The organic phase was washed with brine and dried over MgSO₄. The solvent was removed, yielding the product as a white solid (19.80 g, 75%).

M. p.: 134° C.; $^1$H-NMR (300 MHz, CDCl₃ δ TMS): 2.97 (s, 3 H), 4.04 (s, 2 H), 6.66 (d, J=9 Hz, 2 H), 7.56 (d, J=9 Hz, 2 H).

REFERENCE EXAMPLE 3

4-Methylsulfinylaniline

Following a similar procedure to that described in reference example 1, but starting from 4-methylthioaniline and using 1 equivalent of m-chloroperbenzoic acid, the title compound of the example was obtained as a white solid (80% yield).

$^1$H-NMR (300 MHz, CDCl₃ δ TMS): 2.68 (s, 3 H), 4.02 (s, 2 H), 6.75 (d, J=8.7 Hz, 2 H), 7.45 (d, J=8.7 Hz, 2 H).

REFERENCE EXAMPLE 4

1-(4-Fluorophenyl)-5-(4-methylsulfanylphenyl)imidazole a) N-(4-Methylsulfanylbenzyliden)-4-fluoroaniline A mixture of 10.0 g (90 mmol) of 4-fluoroaniline, 16.5 g (90 mmol) of 4-methylthiobenzaldehyde and 500 mL of benzene was refluxed in a Dean-Stark for 2 days. The solvent was removed and the crude product obtained was directly used in the following reaction.

A sample was recrystallized from Et₂O to give the analytically pure compound.

M. p.: 93° C.; $^1$H-NMR (300 MHz, CDCl₃ δ TMS): 2.54 (s, 3 H), 7.07 (m, 2 H), 7.20 (m, 2 H), 7.31 (d, J=9 Hz, 2 H), 7.79 (d, J=9 Hz, 2 H), 8.38 (s, 1 H).

b) Title Compound 6 g (24.5 mmol) of the above crude product, 3.87 g (24.5 mmol) of benzotriazolylmethylisocyanide and 98 mL of DMSO were placed in a flask and 5.49 g (49 mmol) of potassium tert-butoxide was added. The mixture was heated to 75° C. and, after cooling, Et₂O was added and it was washed with H₂O. The organic phase was dried over MgSO₄ and the solvent was removed, affording a crude product which was chromatographed on silica gel, using EtOAc-hexane mixtures of increasing polarity as eluent. The title compound of the example was obtained as a white solid (4.06 g, 58%).

M. p.: 96–99° C.; $^1$H-NMR (300 MHz, CDCl₃ δ TMS): 2.46 (s, 3 H), 7.0–7.3 (m, 9 H), 7.67 (s, 1 H); Anal ($C_{16}H_{13}FN_2S \cdot 0.5H_2O$) C, H, N, S.

REFERENCE EXAMPLE 5

5-(4-Methylsulfanylphenyl)-1-phenylimidazole

Following a similar procedure to that described in reference example 4, but using aniline instead of 4-fluoroaniline, the title compound of the example was obtained as a white solid (56% yield).

$^1$H-NMR (300 MHz, CDCl₃ δ TMS): 2.46 (s, 3 H), 7.04 (d, J=8.5 Hz, 2 H), 7.12 (d, J=8.5 Hz, 2 H), 7.19 (m, 2 H), 7.25 (s, 1 H), 7.41 (m, 3 H), 7.69 (s, 1 H).

REFERENCE EXAMPLE 6

1-(4-Methylphenyl)-5-(4-methylsulfanylphenyl)imidazole

Following a similar procedure to that described in reference example 4, but using 4-methylaniline instead of 4-fluoroaniline, the title compound of the example was obtained as a white solid (61% yield).

$^1$H-NMR (300 MHz, CDCl₃ δ TMS): 2.39 (s, 3 H), 2.46 (s, 3 H), 7.06 (m, 6 H), 7.18 (m, 3 H), 7.65 (s, 1 H).

REFERENCE EXAMPLE 7

2-Chloro-1-(4-fluorophenyl)-5-(4-methylsulfanylphenyl)imidazole 0.35 mL (2.5 mmol) of diisopropylamine and 8.5 mL of THF were placed in a flask and the mixture was cooled to −20° C. 1.57 mL (2.5 mmol) of a 1.6 M solution of BuLi in hexane was added and after stirring for 10 min, 0.56 g (2 mmol) of the compound obtained in reference example 4 in 14 mL of THF was added. The mixture was stirred for 30 min and 0.78 g (5.8 mmol) of N-chlorosuccinimide in 8 mL of THF was added. The mixture was stirred for 30 min at −20° C. and for 1.5 h at room temperature. The solvent was removed and the residue was dissolved in a EtOAc-H₂O mixture. The layers were separated and the aqueous phase was extracted with EtOAc. The organic phase was dried over MgSO₄ and the solvent was removed yielding a crude product which was chromatographed on silica gel, using EtOAc-hexane mixtures of increasing polarity as eluent. The title compound of the example was obtained as a white solid (0.23 g, 37%).

$^1$H-NMR (300 MHz, CDCl₃ δ TMS): 2.43 (s, 3 H), 6.9–7.2 (m, 8 H), 7.67 (s, 1 H).

REFERENCE EXAMPLE 8

1-(4-Fluorophenyl)-2-methyl-5-(4-methylsulfanylphenyl)imidazole

Following a similar procedure to that described in reference example 7, but using methyl iodide instead of N-chlorosuccinimide, the title compound of the example was obtained as a white solid (30% yield).

$^1$H-NMR (300 MHz, CDCl₃ δ TMS): 2.29 (s, 3 H), 2.43 (s, 3 H), 6.94 (d, J=8.2 Hz, 2 H), 7.03 (d, J=8.2 Hz, 2 H), 7.13 (m, 5 H).

REFERENCE EXAMPLE 9

1-(4-Fluorophenyl)-2-hydroxymethyl-5-(4-methylsulfonylphenyl)imidazole

A mixture of 2.0 g (6.3 mmol) of the compound obtained in example 2 and 10 mL of 40% CH₂O in H₂O was heated at 130° C. for 72 h. The solvent was removed and the residue was dissolved in a EtOAc-H₂O mixture. The layers were separated and the aqueous phase was extracted with EtOAc. The organic phase was dried over MgSO₄ and the solvent was removed, giving a crude product which was chromatographed on silica gel, using EtOAc-hexane mixtures of increasing polarity as eluent. The title compound of the example was obtained as a white solid (0.94 g, 43%).

M. p.: 211–212° C.; $^1$H-NMR (300 MHz, CDCl₃+CD₃OD δ TMS): 3.07 (s, 3 H), 3.8 (s, 1 H+H₂O), 4.45 (s, 2 H), 7.2 (m, 7 H), 7.80 (d, J=8.2 Hz, 2 H); Anal ($C_{17}H_{15}FN_2O_3S$) C, H, N, S.

REFERENCE EXAMPLE 10

2-Bromo-1-(4-fluorophenyl)-5-(4-methylsulfanylphenyl)imidazole

Following a similar procedure to that described in reference example 7, but using N-bromosuccinimide instead of N-chlorosuccinimide, the title compound of the example was obtained as a white solid (40% yield).

$^1$H-NMR (300 MHz, CDCl$_3$ δ TMS): 2.43 (s, 3 H), 6.9–7.2 (m, 9 H).

REFERENCE EXAMPLE 11

2-Chloro-4-(4-methylsulfanylphenyl)-1-phenylimidazole

Following a similar procedure to that described in reference example 7, but starting from the product obtained in reference example 5, the title compound of the example was obtained as a white solid (56% yield).

$^1$H-NMR (300 MHz, CDCl$_3$ δ TMS): 2.43 (s, 3 H), 6.96 (d, J=8.5 Hz, 2 H), 7.08 (d, J=8.5 Hz, 2 H), 7.16 (s, 1 H), 7.22 (m, 2 H), 7.41 (m, 3 H).

REFERENCE EXAMPLE 12

2-Chloro-1-(4-methylphenyl)-5-(4-methylsulfanylphenyl)imidazole

Following a similar procedure to that described in reference example 7, but starting from the product obtained in reference example 6, the title compound of the example was obtained as a white solid (61% yield).

$^1$H-NMR (300 MHz, CDCl$_3$ δ TMS): 2.41 (s, 3 H), 2.44 (s, 3 H), 7.0–7.2 (m, 9 H).

REFERENCE EXAMPLE 13

3-Fluoro-4-methylbenzaldehyde a) Ethyl 3-fluoro-4-methylbenzoate

A mixture of 1 g (6.5 mmol) of 3-fluoro-4-methylbenzoic acid and 4 mL of SOCl$_2$ was refluxed under an argon atmosphere for 2 h. The solvent was removed and the residue was treated with a mixture of 0.64 mL of Et$_3$N and 20 mL of EtOH for 1 h at room temperature. The solvent was removed and the residue was partitioned between CH$_2$Cl$_2$ and H$_2$O. The layers were separated and the aqueous phase was extracted with CH$_2$Cl$_2$. The combined organic phases were dried and an oily residue was obtained, which was used in the next step (100%).

$^1$H-NMR (300 MHz, CDCl$_3$ δ TMS): 1.38 (t, J=7 Hz, 3 H), 2.32 (s, 3 H), 4.37 (q, J=7 Hz, 2 H), 7.25 (m, 1 H), 7.62 (d, J$_{H-F}$=9.4 Hz, 1 H), 7.71 (d, J=7.7 Hz, 1 H).

b) 3-Fluoro-4-methylphenylmethanol

To a mixture of 0.176 g (4.6 mmol) of LiAlH$_4$ and 14 mL of Et$_2$O, 0.5 g (4.6 mmol) of the preceding product dissolved in 28 mL of Et$_2$O was added at 0° C. and under an argon atmosphere, and the mixture was stirred at room temperature for 2 h. 0.28 mL of H$_2$O, 0.6 mL of THF, 0.29 mL of 15% NaOH, 0.8 mL of H$_2$O and Na$_2$SO$_4$ were successively added. After stirring for 10 min the mixture was filtered, washed with Et$_2$O and concentrated, affording 0.3 g of a crude product which was directly used in the next step (93%).

$^1$H-NMR (300 MHz, CDCl$_3$ δ TMS): 2.1 (broad s, 1 H), 2.26 (s, 3 H), 4.62 (s, 2 H), 7.0 (m, 3 H).

c) Title Compound

To a mixture of 0.21 mL (2.3 mmol) of oxalyl chloride and 3 mL of CH$_2$Cl$_2$, a mixture of 0.36 mL (4.7 mmol) of DMSO and 0.7 mL of CH$_2$Cl$_2$ was added at –78° C. and under an argon atmsphere, and it was stirred for 5 min. A mixture of 0.3 g (2.1 mmol) of the preceding product in 0.6 mL of a 1:1 DMSO:CH$_2$Cl$_2$ mixture was added dropwise. The mixture was stirred for 30 min at –71° C. and 2.6 mL (19 mmol) of Et$_3$N was added. The mixture was stirred for 10 min at –78° C. and it was allowed to warm up to room temperature. It was poured over CH$_2$Cl$_2$ and H$_2$O and the layers were separated. The aqueous phase was extracted with CH$_2$Cl$_2$ and the combined organic phases were dried, affording the product as an oil (0.30 g, 100%).

$^1$H-NMR (300 MHz, CDCl$_3$ δ TMS): 2.66 (s, 3 H), 7.29 (m, 1H), 7.44 (d, J$_{H-F}$=9.4 Hz, 1 H), 7.51 (d, J=7.7 Hz, 1 H), 9.87 (s, 1 H).

The method described in reference example 13 is of general use and can be applied to prepare those aldehydes required for the preparation of the compounds of formula I which are not commercially available. The following aldehydes were prepared similarly to reference example 13, but starting from a suitable carboxylic acid.

13(1) 6-Methylpyridyl-3-carboxaldehyde $^1$H-NMR (300 MHz, CDCl$_3$ δ TMS): 2.66 (s, 3 H), 7.32 (d, J=8 Hz, 1 H), 8.06 (d, J=8 Hz, 1 H), 8.95 (s, 1 H), 10.06 (s, 1 H).

13(2) 6-Chloropyridyl-3-carboxaldehyde $^1$H-NMR (300 MHz, CDCl$_3$ δ TMS): 7.51 (d, J=8 Hz, 1 H), 8.14 (d, J=8 Hz, 1 H), 8.87 (s, 1 H), 10.10 (s, 1 H).

13(3) 2,6-Dichloropyridyl-3-carboxaldehyde $^1$H-NMR (300 MHz, CDCl$_3$ δ TMS): 7.43 (d, J=8 Hz, 1 H), 8.18 (d, J=8 Hz, 1 H), 10.35 (s, 1 H).

13(4) 5,6-Dichloropyridyl-3-carboxaldehyde $^1$H-NMR (300 MHz, CDCl$_3$ δ TMS): 8.21 (d, J=1 Hz, 1 H), 8.74 (d, J=1 Hz, 1 H), 10.05 (s, 1 H).

13(5) 3-Methoxy-4-methylbenzaldehyde $^1$H-NMR (300 MHz, CDCl$_3$ δ TMS): 2.29 (s, 3 H), 3.89 (s, 3 H), 7.3 (m, 3H), 9.92 (s, 1H).

13(6) 4-Chloro-3-methylbenzaldehyde $^1$H-NMR (300 MHz, CDCl$_3$ δ TMS): 2.44 (s, 3 H), 7.50 (m, 1 H), 7.66 (m, 1 H), 7.74 (m, 1 H), 9.95 (s, 1 H).

13(7) 4-Ethylsulfanylbenzaldehyde $^1$H-NMR (300 MHz, CDCl$_3$ δ TMS): 1.39 (t, J=7.5 Hz, 3 H), 3.05 (q, J=7.5 Hz, 2 H), 7.34 (d, J=8.5 Hz, 2 H), 7.75 (d, J=8.5 Hz, 2 H), 9.91 (s, 1 H).

EXAMPLE 1

5-(4-Fluorophenyl)-1-(4-methylsulfonylphenyl)imidazole a) N-(4-Fluorobenzyliden)-4-methylsulfonylaniline A mixture of 19.60 g (115 mmol) of 4-methylsulfonylaniline, 12.19 mL (115 mmol) of 4-fluorobenzaldehyde and 590 mL of toluene was refluxed in a Dean-Stark for 2 days. The solvent was removed and the crude product obtained was directly used in the next reaction.

A sample was recrystallized from Et$_2$O to give the analytically-pure compound.

M. p.: 142° C.; $^1$H-NMR (300 MHz, CDCl$_3$ δ TMS): 3.08 (s, 3 H), 7.20 (m, 2 H), 7.30 (m, 2 H), 7.98 (m, 4 H), 8.38 (s, 1 H).

b) Title Compound

A mixture of 31.8 g (115 mmol) of N-(4-fluorobenzyliden)-4-methylsulfonylaniline (obtained in the preceding section), 33.4 g (172 mmol) of tosylmethylisocyanide, 31.7 g (229 mmol) of K$_2$CO$_3$, 795 mL of MeOH and 340 mL of DME was refluxed for 2 h. The solvent was removed and the residue was redissolved in a CH$_2$Cl$_2$/brine mixture and the layers were separated. The aqueous phase was extracted with CH$_2$Cl$_2$ and the combined organic phases were dried over MgSO$_4$ and concentrated. A crude product was obtained, which was washed with Et$_2$O several times to give 29.0 g of a creamy solid. This was recrystallized from EtOAc/hexane (120/25 mL). 27.2 g of the product was obtained as a creamy solid (75%).

M. p.: 151–155° C.; $^1$H-NMR (300 MHz, CDCl$_3$ δ TMS): 3.10 (s, 3 H), 7.05 (m, 2 H), 7.13 (m, 2 H), 7.26 (s, 1 H), 7.36 (d, J=9 Hz, 2 H), 7.75 (s, 1 H), 7.99 (d, J=9 Hz, 2 H); Anal (C$_{16}$H$_{13}$FN$_2$O$_2$S) C, H, N, S.

The following compounds were prepared similarly to example 1, but starting from a suitable aldehyde:

1(1) 5-(4-Methylphenyl)-1-(4-methylsulfonylphenyl)imidazole (81% Yield)

M. p.: 156° C.; $^1$H-NMR (300 MHz, CDCl$_3$ δ TMS): 2.35 (s, 3 H), 3.10 (s, 3 H), 7.01 (d, J=8 Hz, 2 H), 7.11 (d, J=8 Hz, 2 H), 7.26 (s, 1 H), 7.37 (d, J=8.6 Hz, 2 H), 7.74 (s, 1 H), 7.97 (d, J=8.6 Hz, 2 H); Anal (C$_{17}$H$_{16}$N$_2$O$_2$S) C, H, N, S.

1(2) 5-(2,4-Difluorophenyl)-1-(4-methylsulfonylphenyl)imidazole (77% Yield)

M. p.: 119° C.; $^1$H-NMR (300 MHz, CDCl$_3$ δ TMS): 3.09 (s, 3 H), 7.25 (m, 3 H), 7.30 (s, 1 H), 7.33 (d, J=8.6 Hz, 2 H), 7.81 (s, 1 H), 7.98 (d, J=8.6 Hz, 2 H); Anal (C$_{16}$H$_{12}$F$_2$N$_2$O$_2$S) C, H, N, S.

1(3) 1-(4-Methylsulfonylphenyl)-5-phenylimidazole (74% Yield)

M. p.: 164° C.; $^1$H-NMR (300 MHz, CDCl$_3$ δ TMS): 3.09 (s, 3 H), 7.29 (m, 6 H), 7.37 (d, J=8.6 Hz, 2 H), 7.75 (s, 1 H), 7.97 (d, J=8.6 Hz, 2 H); Anal (C$_{16}$H$_{14}$N$_2$O$_2$S.0.5H$_2$O) C, H, N, S.

1(4) 5-(3,4-Dichlorophenyl)-1-(4-methylsulfonylphenyl)lmidazole (81% Yield)

M. p.: 176° C.; $^1$H-NMR (300 MHz, CDCl$_3$ δ TMS): 3.11 (s, 3 H), 6.86 (d, J=8.3 Hz, 1 H), 7.33 (m, 3 H), 7.39 (d, J=8.6 Hz, 2 H), 7.77 (s, 1 H), 8.03 (d, J=8.6 Hz, 2 H); Anal (C$_{16}$H$_{12}$Cl$_2$N$_2$O$_2$S) C, H, N, S.

1(5) 5-(4-Methoxyphenyl)-1-(4-methylsulfonylphenyl)imidazole (57% Yield)

M. p.: 185–187° C.; $^1$H-NMR (300 MHz, CDCl$_3$ δ TMS): 3.09 (s, 3 H), 3.81 (s, 3 H), 6.84 (d, J=8.8 Hz, 2 H), 7.06 (d, J=8.8 Hz, 2 H), 7.21 (s, 1 H), 7.37 (d, J=8.6 Hz, 2 H), 7.72 (s, 1 H), 7.97 (d, J=8.6 Hz, 2 H); Anal (C$_{17}$H$_{16}$N$_2$O$_3$S) C, H, N, S.

1(6) 5-(3-Fuoro-4-methoxyphonyl)-1-(4-methylsulfonylphanyl)imidazole (79% Yield)

M. p.: 166° C.; $^1$H-NMR (300 MHz, CDCl$_3$ δ TMS): 3.10 (s, 3 H), 3.89 (s, 3 H), 6.82 (m, 3 H), 7.23 (s, 1 H), 7.37 (d, J=8.5 Hz, 2 H), 7.73 (s, 1 H), 7.99 (d, J=8.5 Hz, 2 H); Anal (C$_{17}$H$_{15}$FN$_2$O$_3$S.0.5H$_2$O) C, H, N, S.

1(7) 5-(3-Fluorophenyl)-1-(4-methylsulfonylphenyl)imidazole (81% Yield)

$^1$H-NMR (300 MHz, CDCl$_3$ δ TMS): 3.11 (s, 3 H), 6.87 (m, 2 H), 7.02 (m, 1 H), 7.24 (m, 1 H), 7.32 (s, 1 H), 7.39 (d, J=8.5 Hz, 2 H), 7.76 (s, 1 H), 8.01 (d, J=8.5 Hz, 2 H); Anal (C$_{16}$H$_{13}$FN$_2$O$_2$S) C, H, N, S.

1(8) 5-(3-Fluoro-4-methylphenyl)-1-(4-methylsulfonylphenyl)imidazole (51% Yield)

M. p.: 147° C.; $^1$H-NMR (300 MHz, CDCl$_4$ δ TMS): 2.27 (s, 3 H), 3.11 (s, 3 H), 6.76 (m, 2 H), 7.11 (m, 1 H), 7.24 (m, 1 H), 7.38 (d, J=8.5 Hz, 2 H), 7.74 (s, 1 H), 8.05 (d, J=8.5 Hz, 2 H); Anal (C$_{17}$H$_{15}$FN$_2$O$_2$S) C, H, N, S.

1(9) 5-(2-Fluorophenyl)-1(4-methylsulfonylphenyl)imidazole (78% Yield)

M. p.: 188–189° C.; $^1$H-NMR (300 MHz, CDCl$_3$ δ TMS): 3.11 (s, 3 H), 7.00 (t, J=9 Hz, 1 H), 7.17 (m, 1 H), 7.32 (m, 5 H), 7.81 (s, 1 H), 7.95 (d, J=8.6 Hz, 2 H); Anal (C16H$_{13}$FN$_2$O$_2$S.0.25H$_2$O) C, H, N, S.

1(10) 1-(4-Methylsulfonylphenyl)-5-(4-trifluoromethoxyphenyl)imidazole (75% Yield)

M. p.: 141–142° C.; $^1$H-NMR (300 MHz, CDCl$_3$ δ TMS): 3.11 (s, 3 H), 7.16 (s, 4 H), 7.30 (s, 1 H), 7.38 (d, J=8.5 Hz, 2 H), 7.76 (s, 1 H), 8.01 (d, J=8.5 Hz, 2 H); Anal (C$_{17}$H$_{13}$F$_3$N$_2$O$_3$S) C, H, N, S.

1(11) 5-(6-Methyl-3-pyridyl)-1(4-methylsulfonylphanyl)imidazole (73% Yield)

M. p.: 188–193° C.; $^1$H-NMR (300 MHz, CDCl$_3$ δ TMS): 2.55 (s, 3 H), 3.10 (s, 3 H), 7.11 (d, J=8 Hz, 1 H),7.29 (d, J=8 Hz, 1 H), 7.32(s, 1 H), 7.38 (d, J=8.7 Hz, 2 H), 7.78 (s, 1 H), 8.00 (d, J=8.7 Hz, 2 H), 8.32 (s, 1 H); Anal (C$_{16}$H$_{15}$N$_3$O$_2$S.0.25H$_2$O) C, H, N, S.

1(12) 5-(2-Fluoro-4-methoxyphenyl)-1-(4-methylsulfonylphenyl)lm idazole (62% Yield)

M. p.: 183–184° C.; $^1$H-NMR (300 MHz, CDCl$_3$ δ TMS): 3.08 (s, 3 H), 3.81 (s, 3 H), 6.58 (dd, J$_{H-F}$=11.7 Hz, J=2.5 Hz, 1 H), 6.72 (dd, J=8.5 Hz, J=2.5 Hz, 1 H), 7.15 (t, J=8.5 Hz, 1 H), 7.25 (s, 1 H), 7.35 (d, J=8.8 Hz, 2 H), 7.78 (s, 1 H), 7.95 (d, J=8.8 Hz, 2 H); Anal (C$_{17}$H$_{15}$FN$_2$O$_3$S.0.25H$_2$O) C, H, N, S.

1(13) 5-(3-Chloro-4-methylphenyl)-1(4-methylsulfonylphonyl)imidazole (74% Yield)

M. p.: 173–174° C.; $^1$H-NMR (300 MHz, CDCl$_3$ δ TMS): 2.33 (s, 3 H), 3.10 (s, 3 H), 6.77 (m, 1 H), 7.09 (m, 1 H), 7.24 (m, 2 H), 7.39 (d, J=8.5 Hz, 2 H), 7.74 (s, 1 H), 8.01 (d, J=8.5 Hz, 2 H); Anal (C$_{17}$H$_{15}$ClN$_2$O$_2$S.0.25H$_2$O) C, H, N, S.

1(14) 5-(3-Methoxy-4-methylphenyl)-1-(4-methylsulfonylphenyl)imidazole (54% Yield)

M. p.: 174–175° C.; $^1$H-NMR (300 MHz, CDCl$_3$ δ TMS): 2.24 (s, 3 H), 3.14 (s, 3 H), 3.70 (s, 3 H), 6.60 (m, 2 H), 7.09 (m, 1 H), 7.32 (m, 1 H), 7.43 (d, J=8.5 Hz 2 H), 7.79 (s, 1 H), 8.03 (d, J=8.5 Hz, 2 H); Anal (C$_{18}$H$_{18}$N$_2$O$_3$S.0.5H$_2$O) C, H, N, S.

1(15) 5-(4-Chlorophenyl)-1-(4-methylsulfonylphenyl)imidazole (88% Yield)

M. p.: 192–193° C.; $^1$H-NMR (300 MHz, CDCl$_3$ δ TMS): 3.11 (s, 3 H), 7.05 (d, J=8.5 Hz, 2 H), 7.26 (m, 3 H), 7.38 (d, J=8.5 Hz, 2 H), 7.76 (s, 1 H), 8.00 (d, J=8.5 Hz, 2 H); Anal (C16H$_{13}$ClN$_2$O$_2$S.0.75H$_2$O) C, H, N, S.

1(16) 5-(6-Chloro-3-pyridyl)-1-(4-methylsulfonylphenyl)imidazole (69% Yield)

M. p.: 191–192° C.; $^1$H-NMR (300 MHz, CDCl$_3$ δ TMS): 3.11 (s, 3 H), 7.3 (m, 5 H), 7.80 (s, 1 H), 8.03 (d, J=8.5 Hz, 2 H), 8.21 (m, 1 H); Anal (C$_{15}$H$_{12}$ClN$_3$O$_2$S.0.5H$_2$O) C, H, N, S.

1(17) 5-(2,6-Dichloro-3-pyridyl)-1-(4-methylsulfonylphenyl)imidazole (30% Yield, Obtained Together with the Product 1(18) Starting from 2,6dichloropyddyl-3-carboxaldehyde)

$^1$H-NMR (300 MHz, CDCl$_3$ δ TMS); 3.08 (s, 3 H), 7.3 (m, 4 H), 7.58 (d, J=8.5 Hz, 1 H), 7.87 (s, 1 H), 8.03 (d, J=8.5 Hz, 2 H); Anal (C$_{15}$H$_{11}$Cl$_2$N$_3$O$_2$S) C, H, N, S.

1(18) 5-(2-Chloro-6-methoxy-3-pyridyl)-1-(4-methylsulfonylphenyl)imidazole (30% Yield)

M. p.: 192–198° C.; $^1$H-NMR (300 MHz, CDCl$_3$ δ TMS): 3.11 (s, 3 H), 3.95 (s, 3 H), 7.3 (m, 4 H), 7.40 (d, J=8.5 Hz, 1 H), 7.72 (s, 1 H), 8.03 (d, J=8.5 Hz, 2 H).

1(19) 5-(5,6-Dichloro-3-pyridyl)-1-(4-methylsulfonylphenyl)imidazole (52% Yield)

M. p.: 192–198° C.; $^1$H-NMR (300 MHz, CDCl$_3$ δ TMS): 3.11 (S, 3 H), 7.3 (m, 3 H), 7.60 (m, 1 H), 7.81 (s, 1 H), 8.00 (m, 1 H), 8.03 (d, J=8.5 Hz, 2 H); Anal (C$_{15}$H$_{11}$Cl$_2$N$_3$O$_2$S) C, H, N, S.

1(20) 1-(4-Methylsulfonylphenyl)-5-(4-propoxyphenyl)imidazole (60% Yield)

M. p.: 167–169° C.; $^1$H-NMR (300 MHz, CDCl$_3$ δ TMS): 1.04 (t, J=7.5 Hz, 3 H), 1.79 (q, J=7.5 Hz, 2 H), 3.10 (s, 3 H), 3.90 (t, J=7.5 Hz, 2 H), 6.82 (d, J=8.5 Hz, 2 H), 7.02 (d, J=8.5 Hz, 2 H), 7.21 (s, 1 H), 7.36 (d, J=8.5 Hz, 2 H), 7.73 (s, 1 H), 7.95 (d, J=8.5 Hz, 2 H); Anal (C$_{19}$H$_{20}$N$_2$O$_3$S.0.5H$_2$O) C, H, N, S.

1(21) 5-(3,5-Diethoxyphenyl)-1-(4-methylsulfonylphenyl)imidazole (60% Yield)

M. p.: 100–101° C.; $^1$H-NMR (300 MHz, CDCl$_3$ δ TMS): 1.30 (t, J=7.5 Hz, 6 H), 3.08 (s, 3 H), 3.89 (q, J=7.5 Hz, 4 H), 6.23 (m, 2 H), 6.39 (m, 1 H), 7.26 (s, 1 H), 7.39 (d, J=8.5 Hz, 2 H), 7.73 (s, 1 H), 7.99 (d, J=8.5 Hz, 2 H); Anal (C$_{20}$H$_{22}$N$_2$O$_4$S.0.75H$_2$O) C, H, N, S.

1(22) 5-(4-Ethoxyphonyl)-1-(4-methylsulfonylphenyl)imidazole (58% Yield)

M. p.: 165° C.; $^1$H-NMR (300 MHz, CDCl$_3$ δ TMS): 1.41 (t, J=7.5 Hz, 3 H), 3.09 (s, 3 H), 4.0 (q, J=7.5 Hz, 2 H), 6.82 (d, J=8.5 Hz, 2 H), 7.02 (d, J=8.5 Hz, 2 H); 7.21 (s, 1 H), 7.32 (d, J=8.5 Hz, 2 H), 7.72 (s, 1 H), 7.95 (d, J=8.5 Hz, 2 H); Anal (C$_{18}$H$_{18}$N$_2$O$_3$S.0.25H$_2$O) C, H, N, S.

1(23) 1-(4-ethylsulfonylphenyl)-5-(4-nitrophenyl)imidazole (84% Yield)

M. p.: 190–194° C.; $^1$H-NMR (300 MHz, CDCl$_3$ δ TMS): 3.09 (s, 3 H), 7.31 (d, J=8.5 Hz, 2 H), 7.44 (d, J=8.5 Hz, 2 H), 7.52 (s, 1 H), 7.87 (s, 1 H), 8.10 (d, J=8.5 Hz, 2 H), 8.23 (d, J=8.5 Hz, 2 H); Anal (C$_{16}$H$_{13}$N$_3$O$_4$S.0.25H$_2$O) C, H, N, S.

1(24) 5-(4-Methylsulfanylphenyl)-1-(4-methylsulfonylphenyl)imidazole (89% Yield)

M. p.: 153–155° C.; $^1$H-NMR (300 MHz, CDCl$_3$ δ TMS): 2.47 (s, 3 H), 3.09 (s, 3 H), 7.02 (d, J=8.8 Hz, 2 H), 7.15 (d, J=8.8 Hz, 2 H), 7.26 (s, 1 H), 7.37 (d, J=8.6 Hz, 2 H), 7.74 (s, 1 H), 7.98 (d, J=8.6 Hz, 2 H); Anal (C$_{17}$H$_{16}$N$_2$O$_2$S$_2$.0.5H$_2$O) C, H, N, S.

1(25) 5-(4-Ethylsulfanylphenyl)-1-(4-methylsulfonylphonyl)imidazole (57% Yield)

M. p.: 181–185° C.; $^1$H-NMR (300 MHz, CDCl$_3$ δ TMS): 1.32 (t, J=7.5 Hz, 3 H), 2.95 (q, J=7.5 Hz, 2 H), 3.11 (s, 3 H), 7.02 (d, J=8.5 Hz, 2 H), 7.24 (m, 3 H), 7.38 (d, J=8.5 Hz, 2 H), 7.76 (m, 1 H), 8.00 (d, J=8.5 Hz, 2 H); Anal (C$_{18}$H$_{18}$N$_2$O$_2$S$_2$) C, H, N. S.

1(26) 5-(4-Dimethylaminophenyl)-1-(4-methylsulfonylphenyl)imidazole (50% Yield)

$^1$H-NMR (300 MHz, CDCl$_3$ δ TMS): 2.96 (s, 6 H), 3.09 (s, 3 H), 6.61 (d, J=8.8 Hz, 2 H), 6.97 (d, J=8.8 Hz, 2 H), 7.17 (s, 1 H), 7.39 (d, J=8.6 Hz, 2 H), 7.71 (s, 1 H), 7.95 (d, J=8.6 Hz, 2 H).

EXAMPLE 2

1-(4-Fluorophenyl)-5-(4-methylsulfonylphenyl)imidazole

Following a similar procedure to that described in example 1, but starting from the compound obtained in reference example 1 and 4-fluoroaniline, the title compound of the example was obtained as a white solid (70% yield).

M. p.: 133–134° C.; $^1$H-NMR (300 MHz, CDCl$_3$ δ TMS): 3.05 (s, 3 H), 7.20 (m, 4 H), 7.31 (d, J=9 Hz, 2 H), 7.41 (s, 1 H), 7.73 (s, 1 H), 7.83 (d, J=9 Hz, 2 H); Anal (C$_{16}$H$_{13}$FN$_2$O$_2$S) C, H, N, S.

EXAMPLE 3

5-(4-Fluorophenyl)-4-methyl-1-(4-methylsulfonylphenyl)imidazole

Following a similar procedure to that described in example 1, but using α-tosylethylisocyanide instead of tosylmethylisocyanide, the title compound of the example was obtained as a white solid (45% yield).

M. p.: 143–143° C.; $^1$H-NMR (300 MHz, CDCl$_3$ δ TMS): 2.31 (s, 3 H), 3.08 (s, 3 H), 7.05 (m, 4 H), 7.27 (d, J=9 Hz, 2 H), 7.71 (s, 1 H), 7.93 (d, J=9 Hz, 2 H); Anal (C$_{17}$H$_{15}$FN$_2$O$_2$S.0.25H$_2$O) C, H, N, S.

EXAMPLE 4

4-Chloro-5-(4-fluorophenyl)-1-(4-methylsulfonylphenyl)imidazole

A mixture of 27.2 g (86 mmol) of 5-(4-fluorophenyl)-1-(4-methylsulfonylphenyl)imidazole (obtained in example 1), 12.05 g (90 mmol) of N-chlorosuccinimide and 81 mL of CHCl$_3$ was refluxed for 18 h. The solvent was removed and the residue was redissolved in CH$_2$Cl$_2$ and washed with 1 N HCl and next with 1 N NaOH and brine. The organic phase was dried over MgSO$_4$ and concentrated. The crude product obtained was washed with Et$_2$O several times to afford 26.2 g of a creamy solid, which was chromatographed on silica gel, using EtOAc-hexane mixtures of increasing polarity as eluent. The title compound of the example was obtained as a white solid (24.0 g, 80%).

M. p.: 167° C.; $^1$H-NMR (300 MHz, CDCl$_3$ δ TMS): 3.13 (s, 3 H), 7.12 (m, 2 H), 7.20 (m, 2 H), 7.32 (d, J=9 Hz, 2 H), 7.71 (s, 1 H), 8.02 (d, J=9 Hz, 2 H); Anal (C$_{16}$H$_{12}$ClFN$_2$O$_2$S) C, H, N, S.

The following compounds were prepared similarly to example 4, but starting from the corresponding imidazole:

4(1) 4-Chloro-5-(4-methylphenyl)-1-(4-methylsulfonylphenyl)imidazole (90% Yield)

Starting from Example 1(1)

M. p.: 182° C.; $^1$H-NMR (300 MHz, CDCl$_3$ δ TMS): 2.36 (s, 3 H), 3.08 (s, 3 H), 7.07 (d, J=8.1 Hz, 2 H), 7.16 (d, J=8.1 Hz, 2H), 7.32 (d, J=8.6 Hz, 2 H), 7.65 (s, 1 H), 7.96 (d, J=8.6 Hz, 2 H); Anal (C$_{17}$H$_{15}$ClN$_2$O$_2$S.0.25H$_2$O) C, H, N, S.

4(2) 4-Chloro-5-(2,4-difluorophonyl)-1-(4-methylsulfonylphenyl)imidazole (45% Yield)

Starting from Example 1(2)

M. p.: 183–184° C.; $^1$H-NMR (300 MHz, CDCl$_3$ δ TMS): 3.08 (s, 3 H), 6.79 (m, 1 H), 7.00 (m, 1 H), 7.31 (d, J=8.4 Hz, 2 H), 7.40 (m, 1 H), 7.72 (s, 1 H), 7.97 (d, J=8.4 Hz, 2 H); Anal (C$_{16}$H$_{11}$ClF$_2$N$_2$O$_2$S) C, H, N, S.

4(3) 4-Chloro-1-(4-methylsulfonylphenyl)-5-phenylimidazole (51% Yield)

Starting from Example 1(3)

M. p.: 145–146° C.; $^1$H-NMR (300 MHz, CDCl$_3$ δ TMS): 3.08 (s, 3 H), 7.1–7.4 (m, 7 H), 7.66 (s, 1 H), 7.95 (d, J=8.6 Hz, 2 H); Anal (C$_{16}$H$_{13}$ClN$_2$O$_2$S.0.25H$_2$O) C, H, N, S.

4(4) 4-Chloro-5-(3,4-dichlorophenyl)-1(4-methylsulfonylphenyl)imidazole (74% Yield)

Starting from Example 1(4)

M. p.: 156–157° C.; $^1$H-NMR (300 MHz, CDCl$_3$ δ TMS): 3.10 s, 3 H), 6.95 (d, J=8.3 Hz, 1 H), 7.34 (d, J=8.4 Hz, 2 H), 7.37 (m, 2 H), 7.68 (s, 1 H), 8.02 (d, J=8.4 Hz, 2 H); Anal (C$_{16}$H$_{11}$Cl$_3$N$_2$O$_2$S) C, H, N, S.

4(5) 4-Chloro-5-(4-methoxyphenyl)-1-(4-methylsulfonylphenyl)imidazole (63% Yield)

Starting from Example 1(5)

M. p.: 205° C.; $^1$H-NMR (300 MHz, CDCl$_3$ δ TMS): 3.08 (s, 3 H), 3.82 (s. 3 H), 6.88 (d, J=8.7 Hz, 2 H), 7.12 (d, J=8.7 Hz, 2 H), 7.31 (d, J=8.5 Hz, 2 H), 7.64 (s, 1 H), 7.96 (d, J=8.5 Hz, 2 H); Anal (C$_{17}$H$_{15}$ClN$_2$O$_3$S.0.5H$_2$O) C, H, N, S.

4(6) 4-Chloro-5-(3-fluoro-4-methoxyphenyl)-1-(4-methylsulfonylphenyl)-imidazole (73% Yield)

Starting from Example 1(6)

M. p.: 196° C.; $^1$H-NMR (300 MHz, CDCl$_3$ δ TMS): 3.09 (s, 3 H), 3.91 (s, 3 H), 6.92 (m, 3 H), 7.33 (d, J=9 Hz, 2 H), 7.64 (s, 1 H), 7.99 (d, J=9 Hz, 2 H); Anal (C$_{17}$H$_{14}$ClFN$_2$O$_3$S) C, H, N, S.

4(7) 4-Chloro-5-(3-fluorophonyl)-1-(4-methylsulfonylphonyl)imidazole (62% Yield)

Starting from Example 1(7)

M. p.: 167–179° C.; $^1$H-NMR (300 MHz, CDCl$_3$+CD$_3$OD δ TMS): 3.07 (s, 3 H), 6.92 (m, 2 H), 7.06 (m, 1 H), 7.29 (m, 1 H), 7.40 (d, J=8.6 Hz, 2 H), 7.97 (d, J=8.6 Hz, 2 H), 8.36 (s, 1 H); Anal (C$_{16}$H$_{12}$ClFN$_2$O$_2$S.HCl) C, H, N, S.

4(8) 4-Chloro-5-(3-fluoro-4-methylphenyl)-1-(4-methylsulfonylphenyl)-imidazole (48% Yield)

Starting from Example 1(8)

M. p.: 176° C.; $^1$H-NMR (300 MHz, CDCl$_3$ δ TMS): 2.30 (s, 3 H), 3.10 (s, 3 H), 6.84 (d, J=7.7 Hz, 1 H), 6.93 (d, J=9.7 Hz, 1 H), 7.19 (t, J=7.7 Hz, 1 H), 7.57 (d, J=87.8 Hz, 2 H), 8.02 (d, J=7.8 Hz, 2 H), 9.26 (s, 1 H): Anal (C$_{17}$H$_{14}$ClFN$_2$O$_2$S.HCl) C, H, N, S.

4(9) 4-Chloro-5-(2-fluorophenyl)-1-(4-methylsulfonylphonyl)imidazole (65% Yield)

Starting from Example 1(9)

M. p.: 177–178° C.; $^1$H-NMR (300 MHz, CDCl$_3$+CD$_3$OD δ TMS): 3.12 (s, 3 H), 7.07 (m, 1 H), 7.29 (m, 1 H), 7.42 (m, 2 H), 7.45 (d, J=8.6 Hz, 2H), 7.99 (d, J=8.6 Hz, 2 H), 8.55 (s, 1 H); Anal (C$_{16}$H$_{12}$ClFN$_2$O$_2$S.HCl.0.5H$_2$O) C, H, N, S.

4(10) 4-Chloro-1-(4-methylsulfonylphenyl)-5-(4-trifluoromethoxyphenyl)-imidazole (73% Yield)

Starting from Example 1(10)

M. p.: 136–138° C.; $^1$H-NMR (300 MHz, CDCl$_3$ δ TMS): 3.10 (s, 3 H), 726 (m, 4 H), 7.54 (d, J=8 Hz, 2 H), 8.02 (d, J=8 Hz, 2 H), 8.98 (s, 1 H); Anal (C$_{17}$H$_{12}$ClF$_3$N$_2$O$_3$S.HCl) C, H, N, S.

4(11) 4-Chloro-5-(6-methyl-3-pyridyl)-1-(4-methylsulfonylphenyl)imidazole (63% Yield) ps Starting from Example 1(11)

$^1$H-NMR (300 MHz, CDCl$_3$+CD$_3$OD δ TMS): 2.87 (s, 3 H), 3.13 (s, 3 H), 7.47 (d, J=8.5 Hz, 2 H), 7.73 (d, J=8.3 Hz, 1 H), 7.94 (s, 1 H), 8.04 (d, J=8.5 Hz, 2 H), 8.08 (d, J=8.3 Hz, 1 H), 8.56 (s, 1 H); Anal (C$_{16}$H$_{14}$ClN$_3$O$_2$S.2HCl.0.5H$_2$O) C, H, N, S.

4(12) 4-Chloro-5-(2-fluoro-4-methoxyphenyl)-1-(4-methylsulfonylphenyl)-imidazole (61% Yield)

Starting from Example 1(12)

M. p.: 176–198° C.; $^1$H-NMR (300 MHz, CDCl$_3$ δ TMS): 3.09 (s, 3 H), 3.83 (s, 3 H), 6.58 (d, J$_{H-F}$=11.6 Hz, 1 H), 6.79 (d, J=8.5 Hz, 1 H), 7.30 (m, 1 H), 7.54 (m, 2 H), 8.00 (d, J=8 Hz, 2 H), 9.21 (s, 1 H); Anal (C$_{17}$H$_{14}$ClFN$_2$O$_3$S.HCl.0.25H$_2$O) C, H, N,S.

4(13) 4-Chloro-5-(3-chloro-4-methylphenyl)-1-(4-methylsulfonylphenyl)-imidazole (76% Yield)

Starting from Example 1(13)

M. p.: 181–182° C.; $^1$H-NMR (300 MHz, CDCl$_3$ δ TMS): 2.35 (s, 3 H), 3.11 (s, 3 H), 6.90 (m, 1 H), 7.17 (m, 1 H), 7.31 (m, 1 H), 7.50 (d, J=8.5 Hz, 2 H), 8.01 (d, J=8.5 Hz, 2 H), 8.90 (s, 1 H); Anal (C$_{17}$H$_{14}$Cl$_2$N$_2$O$_2$S.HCl) C, H, N, S.

4(14) 4-Chloro-5-(3-methoxymethylphenyl)-1-(4-methylsulfonylphenyl)-imidazole (71% Yield)

Starting from Example 1(14)

M. p.: 178° C.; $^1$H-NMR (300 MHz, CDCl$_3$ δ TMS): 2.22 (s, 3 H), 3.14 (s, 3 H), 3.78 (s, 3 H), 6.64 (m, 2 H), 7.09 (m, 1 H), 7.58 (m, 2 H), 8.03 (d, J=8.5 Hz, 2 H), 9.31 (s, 1 H); Anal (C$_{18}$H$_{17}$ClN$_2$O$_3$S.HCl) C, H, N, S.

4(15) 4-Chloro-5-(4-chlorophenyl)-1-(4-methylsulfonylphenyl)imidazole (55% Yield)

Starting from Example 1(15)

M. p.: 222–223° C.; $^1$H-NMR (300 MHz, CDCl$_3$+CD$_3$OD δ TMS): 3.13 (s, 3 H), 7.16 (d, J=8.3 Hz, 2H), 7.38 (m, 4H), 8.01 (m, 3H); Anal (C$_{16}$H$_{12}$Cl$_2$N$_2$O$_2$S.HCl.0.25H$_2$O) C, H, N, S.

4(16) 4-Chloro-5-(6-chloro-3-pyridyl)-1-(4-methylsulfonylphenyl)imidazole (45% Yield)

Starting from Example 1(16)

M. p.: 223°C.; $^1$H-NMR (300 MHz, CDCl$_3$+CD$_3$OD δ TMS): 3.07 (s, 3 H), 7.3 (m, 3 H), 7.51 (m, 1 H), 7.97 (m, 3 H), 8.17 (m, 1 H); Anal (C$_{15}$H$_{11}$Cl$_2$N$_3$O$_2$S.2HCl) C, H, N, S.

4(17) 4-Chloro-2,6-dichloro-3-pyridyl)-1-(4-methylsulfonylphenyl)imidazole

Starting from Example 1(17)

M. p.: 253° C.; $^1$H-NMR (300 MHz, CDCl$_3$ δ TMS): 3.10 (s, 3 H), 7.26 (d, J=8.5 Hz, 2 H); 7.40 (d, J=8.5 Hz, 1 H), 7.70 (d, J=8.5 Hz, 1 H), 7.77 (s, 1 H), 7.99 (d, J=8.5 Hz, 2 H); Anal (C$_{15}$H$_{10}$Cl$_3$N$_3$O$_2$S.0.5H$_2$O) C, H, N, S.

4(18) 4-Chloro-5-(2-chloro-6-methoxy-3-pyridyl)-1-(4-methylsulfonylphonyl)-imidazole Starting from Example 1(18)

$^1$H-NMR (300 MHz, CDCl$_3$+CD$_3$OD δ TMS): 3.06 (s, 3 H), 3.91 (s, 3 H), 6.73 (d, J=8.5 Hz, 1 H), 7.35 (m, 2 H), 7.52 (d, J=8 Hz, 1 H), 7.94 (m, 3 H); Anal (C$_{16}$H$_{13}$Cl$_2$N$_3$O$_3$S.HCl) C, H, N, S.

4(19) 4-Chloro-5-(5,6-dichloro-3-pyridyl)-1-(4-methylsulfonylphenyl)imidazole (50% Yield)

Starting from Example 1(19)

M. p.: 223–230° C.; $^1$H-NMR (300 MHz, CDCl$_3$ δ TMS): 3.12 (s, 3 H), 7.37 (d, J=8.4 Hz, 2H), 7.72 (s, 1H), 7.76 (s, 1H), 8.02 (s, 1H), 8.07 (d, J=8.4 Hz, 2H); Anal (C15H$_{10}$Cl$_3$N$_3$O$_2$S.0.5H$_2$O) C, H, N, S.

4(20) 4-Chloro-1-(4-methylsulfonylphenyl)-5(4-propoxyphenyl)imidazole (60% Yield)

Starting from Example 1(20)

M. p.: 161–163° C.; $^1$H-NMR (300 MHz, CDCl$_3$ δ TMS): 1.04 (t, J=7.5 Hz, 3 H), 1.79 (q, J=7.5 Hz, 2 H), 3.10 (s, 3 H), 3.92 (t, J=7.5 Hz, 2 H), 6.88 (d, J=8.5 Hz, 2 H), 7.10 (d, J=8.5 Hz, 2 H), 7.60 (d, J=8.5 Hz, 2 H), 8.00 (d, J=8.5 Hz, 2 H), 9.58 (s, 1 H); Anal (C$_{19}$H$_{19}$ClN$_2$O$_3$S.HCl.0.5H$_2$O) C, H, N, S.

4(21) 4-Chloro-5-(3,5-diethoxyphenyl)-1-(4-methylsulfonylphenyl)imidazole (60% Yield)

Starting from Example 1(21)

M. p.: 227–231° C.; $^1$H-NMR (300 MHz, CDCl$_3$ δ TMS): 1.38 (t, J=7.5 Hz, 3 H), 1.42 (t, J=7.5 Hz, 3 H), 3.08 (s, 3 H), 3.94 (q, J=7.5 Hz, 2 H), 4.03 (q, J=7.5 Hz, 2 H), 6.50 (m, 1 H), 6.56 (m, 1 H), 7.52 (s, 1 H), 7.66 (d, J=8.5 Hz, 2 H), 8.00 (d, J=8.5 Hz, 2 H), 10.08 (s, 1 H); Anal (C$_{20}$H$_{21}$ClN$_2$O$_4$S.HCl) C, H, N, S.

4(22) 4-Chloro-5-(4-ethoxyphenyl)-1-(4-methylsulfonylphenyl)imidazole (65% Yield)

Starting from Example 1(22)

M. p.: 207° C.; $^1$H-NMR (300 MHz, CDCl$_3$ δ TMS): 1.41 (t, J=7.5 Hz, 3 H), 3.13 (s, 3 H), 4.08 (q, J=7.5 Hz, 2 H), 6.90 (d, J=8.5 Hz, 2 H), 7.12 (d, J=8.5 Hz, 2 H), 7.50 (d, J=8.5 Hz, 2 H), 8.02 (d, J=8.5 Hz, 2 H), 9.12 (s, 1 H); Anal (C$_{18}$H$_{17}$ClN$_2$O$_3$S.HCl) C, H, N, S.

4(23) 4-Chloro-1-(4-methylsulfonylphonyl)-5(4-nitrophenyl)imidazole (56% Yield)

Starting from Example 1(23)

M. p.: 211–217° C.; $^1$H-NMR (300 MHz, CDCl$_3$ δ TMS): 3.09 (s, 3 H), 7.34 (d, J=8.5 Hz, 2 H), 7.39 (d, J=8.5 Hz, 2 H), 7.72 (s, 1 H), 8.02 (d, J=8.5 Hz, 2 H), 8.20 (d, J=8.5 Hz, 2 H); Anal (C$_{16}$H$_{12}$ClN$_3$O$_4$S) C, H, N, S.

4(24) 4-Chloro-5-(4-methylsulfanylphenyl)-1-(4-methylsulfonylphenyl)-imidazole (18% Yield)

Starting from Example 1(24)

M. p.; 216–220° C.; $^1$H-NMR (300 MHz, CDCl$_3$ δ TMS): 2.50 (s, 3 H), 3.10 (s, 3 H), 7.11 (d, J=8.8 Hz, 2 H), 7.21 (d, J=8.8 Hz, 2 H), 7.35 (d, J=8.6 Hz, 2 H), 7.66 (s, 1 H), 7.99 (d, J=8.6 Hz, 2 H); Anal (C$_{17}$H$_{15}$ClN$_2$O$_2$S$_2$) C, H, N, S.

4(25) 4-Chloro-5-(4-ethylsulfanylphenyl)-1-(4-methylsulfonylphenyl)imidazole (21% Yield)

Starting from Example 1(25)

M. p.: 181–185° C.; $^1$H-NMR (300 MHz, CDCl$_3$ δ TMS): 1.35 (t, J=7.5 Hz, 3 H), 2.99 (q, J=7.5 Hz, 2 H), 3.10 (s, 3 H), 7.09 (d, J=8.5 Hz, 2 H), 7.24 (d, J=8.5 Hz, 2 H), 7.32 (d,

J=8.5 Hz, 2 H), 7.66 (m, 1 H), 8.00 (d, J=8.5 Hz, 2 H); Anal ($C_{18}H_{17}ClN_2O_2S_2$) C, H, N, S.

4(26) 4-Chloro-5-(6-ethoxy-3-pyridyl)-1-(4-methylsulfonylphonyl)imidazole (50% Yield)

Starting from Example 16

M. p.: 186–188° C.; $^1$H-NMR (300 MHz, CDCl$_3$ δ TMS): 1.25 (t, J=7.5 Hz, 3 H), 3.11 (s, 3 H), 4.38 (q, J=7.5 Hz, 2 H), 6.73 (d, J=8.5 Hz, 1 H), 7.38 (m, 3 H), 7.69 (m, 1 H), 8.02 (m, 3 H); Anal ($C_{17}H_{16}ClN_3O_3S$) C, H, N, S.

EXAMPLE 5

4-Bromo-5-(4-fluorophenyl)-1-(4-methylsulfonylphenyl)imidazole

To a solution of 0.21 g (0.66 mmol) of the compound obtained in example 1 in 16 mL of CHCl$_3$, a solution of 0.051 mL (1 mmol) of Br$_2$ in 16 mL of CHCl$_3$ was added dropwise and the mixture is stirred for 15 min. A suspension was obtained, which was dissolved by adding CHCl$_3$ and was then washed with 1 N NaOH and H$_2$O. It was dried over MgSO$_4$ and the solvent was removed, affording a crude product which was chromatographed on silica gel, using EtOAc-hexane mixtures of increasing polarity as eluent. The title compound of the example was obtained as a white solid (0.11 g, 41%).

M. p.: 148° C.; $^1$H-NMR (300 MHz, CDCl$_3$ δ TMS): 3.08 (s, 3 H), 7.06 (m, 2 H), 7.20 (m, 2 H), 7.30 (d, J=9 Hz, 2 H), 7.71 (s, 1 H), 8.97 (d, J=9 Hz, 2 H); Anal ($C_{16}H_{12}BrFN_2O_2S$) C, H, N, S.

EXAMPLE 6

1-(4-Fluorophenyl)-2-methyl-5-(4-methylsulfonylphenyl)imidazole

Following a similar procedure to that described in reference example 1, but starting from the compound obtained in reference example 8, the title compound of the example was obtained as a white solid (80% yield).

M. p.: 160–162° C.; $^1$H-NMR (300 MHz, CDCl$_3$ δ TMS): 2.32 (s, 3 H), 3.03 (s,3 H), 7.1 (m, 6 H), 7.31 (s, 1 H), 7.76 (d, J=8.5 Hz, 2 H); Anal ($C_{17}H_{15}FN_2O_2S.0.5H_2O$) C, H, N, S.

EXAMPLE 7

2Chloro-1-(4-fluorophenyl)-5-(4-methylsulfonylphenyl)imidazole

Following a similar procedure to that described in reference example 1, but starting from the compound obtained in reference example 7, the title compound of the example was obtained as a white solid (80% yield).

M. p.: 218–220° C.; $^1$H-NMR (300 MHz, CDCl$_3$ δ TMS): 3.04 (s, 3 H), 7.1 (m, 6 H), 7.32 (s, 1 H), 7.82 (d, J=8.5 Hz, 2 H); Anal ($C_{16}H_{12}Cl_2FN_2O_2S.0.25H_2O$) C, H, N, S.

EXAMPLE 8

1-(4-Fluorophenyl)-5-(4-methylsulfonylphenyl)imidazol-2-carboxaldehyde (8a) and methyl 1-(4-fluorophenyl)-5-(4-methylsulfonylphenyl)imidazol-2carboxylate (8b)

A mixture of 0.2 g (0.6 mmol) of the compound obtained in reference example 9, 1.26 g (14.5 mmol) of MnO$_2$, 0.100 g 3 Å molecular sieve, 6.5 mL of MeOH and 4 mL of THF was stirred at room temperature for 24 h. The resulting suspension was filtered through celite, and washed with plentiful hot THF. The solvent was removed and the crude product obtained was chromatographed on silica gel, using EtOAc-hexane mixtures of increasing polarity as eluent. The following compounds were obtained:

8a: (0.073 g, 36%); M. p.: 198° C.; $^1$H-NMR (300 MHz, CDCl$_3$ δ TMS): 3.05 (s, 3 H), 7.1 (m, 6 H), 7.62 (s, 1 H), 7.85 (d, J=8.5 Hz, 2 H), 9.84 (s, 1 H); Anal ($C_{17}H_{13}FN_2O_3S.0.5H_2O$) C, H, N, S.

8b: (0.061 g, 28%); M. p.: 192–194° C.; $^1$H-NMR (300 MHz, CDCl$_3$ δ TMS): 3.03 (s, 3 H), 3.87 (s, 3 H), 7.1 (m, 6 H), 7.50 (s, 1 H), 7.87 (d, J=8.5 Hz, 2 H); Anal ($C_{18}H_{15}FN_2O_4S.1.25H_2O$) C, H, N, S.

EXAMPLE 9

2-Bromo-1-(4-fluorophenyl)-5-(4-methylsulfonylphenyl)imidazole

Following a similar procedure to that described in reference example 1, but starting from the compound obtained in reference example 10, the title compound of the example was obtained as a white solid (80% yield).

M. p.: 207–208° C.; $^1$H-NMR (300 MHz, CDCl$_3$ δ TMS): 3.05 (s, 3 H), 7.1 (m, 6 H), 7.37 (s, 1 H), 7.80 (d, J=8.5 Hz, 2 H); Anal ($Cr_6Hl_2BrFN_2O_2S$) C, H. N, S.

EXAMPLE 10

1-(4-Fluorophenyl)-5-(4-methylsulfonylphenyl)imidazol-2-carbonitrile

A mixture of 0.24 g (0.7 mmol) of the compound obtained in example 8a, 0.155 g (1.4 mmol) of hydroxylamine-O-sulfonic acid, 3 mL of pyridine and 30 mL of EtOH was stirred at reflux for 18 h. The mixture was poured over CHCl$_3$ and washed with saturated NaHCO$_3$ solution. It was dried over MgSO$_4$ and the solvent was removed, affording a crude product which was chromatographed on silica gel, using EtOAc-hexane mixtures of increasing polarity as eluent. The title compound of the example was obtained as a white solid (0.090 g, 37%).

M. p.: 192° C.; $^1$H-NMR (300 MHz, CDCl$_3$+CD$_3$OD δ TMS): 2.99 (s, 3 H), 7.1 (m, 6 H), 7.39 (s, 1 H), 7.75 (d, J=8.5 Hz, 2 H); Anal ($C_{17}H_{12}FN_3O_2S.0.25H_2O$) C, H, N, S.

EXAMPLE 11

2-Chloro-5-(4-methylsulfonylphenyl)-1-phenylimidazole

Following a similar procedure to that described in reference example 1, but starting from the compound obtained in reference example 11, the title compound of the example was obtained as a white solid (49% yield).

M. p.: 185–193° C.; $^1$H-NMR (300 MHz, CDCl$_3$ δ TMS): 3.01 (s, 3 H), 7.22 (m, 5 H), 7.50 (m, 3 H), 7.77 (d, J=8.5 Hz, 2 H); Anal ($C_{16}H_{13}ClN_2O_2S.0.75H_2O$) C, H, N, S.

EXAMPLE 12

2-Chloro-1-(4-methylphenyl)-5-(4-methylsulfonylphenyl)imidazole

Following a similar procedure to that described in reference example 1, but starting from the compound obtained in reference example 12, the title compound of the example was obtained as a white solid (60% yield).

M. p.: 156–160° C.; $^1$H-NMR (300 MHz, CDCl$_3$ δ TMS): 2.39 (s, 3 H), 3.02 (s, 3 H), 7.05 (d, J=8.5 Hz, 2 H), 7.3 (m, 5 H), 8.05 (d, J=8.5 Hz, 2 H); Anal ($C_{17}H_{15}ClN_2O_2S.0.25H_2O$) C, H, N, S.

EXAMPLE 13

4-[4-Chloro-5-(4-fluorophenyl)imidazol-1-yl]benzenesulfonamide a) N-(4-Fluorobenzyliden)-4-methylsulfinylaniline A mixture of 3.0 g (19 mmol) of 4-methylsulfinylaniline (obtained in reference example 3), 2 mL (19 mmol) of 4-fluorobenzaldehyde and 80 mL of benzene was refluxed in a Dean-Stark for 2 days. The solvent was removed and the crude product obtained was directly used in the next reaction.

$^1$H-NMR (300 MHz, CDCl$_3$ δ TMS): 2.75 (s, 3 H), 7.18 (m, 2 H), 7.32 (m, 2 H), 7.68 (d, J=8.5 Hz, 2 H), 7.91 (m, 2 H), 8.41 (s, 1 H).

b) 5-(4-Fluorophenyl)-1-(4-methylsulfinylphenyl)imidazole

A mixture of the preceding crude product, 5.65 g (29 mmol) of tosylmethylisocyanide, 5.33 g (39 mmol) of K$_2$CO$_3$, 134 mL of MeOH and 58 mL of DME was refluxed for 2 h. The solvent was removed and the residue was redissolved in a CH$_2$Cl$_2$/brine mixture and the layers were separated. The aqueous phase was extracted with CH$_2$Cl$_2$ and the combined organic phases were dried over MgSO$_4$ and concentrated. A crude product was obtained, which was washed with Et$_2$O several times to afford 3.5 g of the product as a creamy solid (60%).

$^1$H-NMR (300 MHz, CDCl$_3$ δ TMS): 2.77 (s, 3 H), 6.99 (m, 2 H), 7.10 (m, 2 H), 7.25 (s, 1 H), 7.33 (d, J=8.5 Hz, 2 H), 7.69 (d, J=8.5 Hz, 2 H), 7.73 (s, 1 H).

c) 1-[4-(Acetoxymethylsulfanyl)phenyl]-5-(4-fluorophenyl)imidazole 1.60 g (5.3 mmol) of the preceding product, 16 mL of Ac$_2$O and 1.6 g (20 mmol) of NaOAc were placed in a flask under a nitrogen atmosphere and the mixture was refluxed for 8 h. The solvent was removed and the crude product was chromatographed on silica gel using EtOAc/hexane mixtures of increasing polarity as eluent, to afford 1.6 g of the product as a foamy solid (84%).

$^1$H-NMR (300 MHz, CDCl$_3$ δ TMS): 2.11 (s, 3 H), 5.44 (s, 2 H), 6.99 (m, 2 H), 7.10 (m, 2 H), 7.14 (s, 1 H), 7.25 (d, J=8.5 Hz, 2 H), 7.47 (d, J=8.5 Hz, 2 H), 7.72 (s, 1 H).

d) 1-[4-(Acetoxymethylsulfanyl)phenyl]-4-chloro-5-(4-fluorophenyl)imidazole

Following a similar procedure to that described in example 4, but starting from the product obtained in section c, the desired compound was obtained (0.9 g, 51%).

$^1$H-NMR (300 MHz, CDCl$_3$ δ TMS): 2.11 (s, 3 H), 5.43 (s, 2 H), 7.05 (m, 4 H), 7.19 (m, 2 H), 7.44 (d, J=8.6 Hz, 2 H), 7.59(s, 1 H).

e) Sodium [4-chloro-5-(4-fluorophonyl)imidazol-1-yl]benzenesulfinate

The preceding crude product, 8 mL of CH$_2$Cl$_2$ and 4 mL of MeOH were placed in a flask and the mixture was cooled to 0° C. 1.5 g (2.6 mmol) of magnesium monoperoxyphthalate hexahydrate was added and the mixture was stirred overnight at room temperature. 12 mL of 5% NaHCO$_3$ was added and the mixture was extracted with CH$_2$Cl$_2$. The solvent was removed and the residue was dissolved in a mixture of 8 mL of THF and 4 mL of MeOH and was then cooled to 0° C. 2.56 mL of 1 N NaOH was added and the mixture was stirred for 1 h at room temperature and was then concentrated by removing H$_2$O by azeotropic distillation with EtOH/toluene mixtures. The residue was dried in vacuo, yielding 0.90 g of a crude product, which was directly used in the next step.

$^1$H-NMR (300 MHz, CDCl$_3$+CD$_3$OD δ TMS): 6.99 (m, 2 H), 7.18 (m, 4 H), 7.63 (s, 1 H), 7.68 (d, J=8.2 Hz, 2 H).

f) Title Compound

The preceding crude product, 13 mL of H$_2$O, 0.21 g (2.7 mmol) of NaOAc and 0.30 g (2.7 mmol) of hydroxylamine-O-sulfonic acid were placed in a flask and the mixture was stirred overnight at room temperature. The resulting suspension was filtered and the solid was washed with EtOAc and H$_2$O. The layers were separated and the aqueous phase was extracted with EtOAc. The combined organic phases were concentrated and the residue was chromatographed on silica gel using hexane-EtOAc mixtures of increasing polarity as eluent. 0.420 g of the product was obtained as a yellow solid (48% yield).

M. p.: 223° C.; $^1$H-NMR (300 MHz, CDCl$_3$ δ TMS): 4.84 (s, 2 H), 7.05 (m, 2 H), 7.18 (m, 2 H), 7.26 (d, J=8.7 Hz, 2 H), 7.65 (s, 1 H), 7.96 (d, J=8.7 Hz, 2 H); Anal (C$_{15}$H$_{11}$ClFN$_3$O$_2$S.0.25H$_2$O) C, H, N, S.

The following compounds were prepared similarly to example 13, but starting from the corresponding aldehyde:

13(1) 4-(4-Chloro-5-phenylimidazol-1-yl)benzenesulfonamide

M. p.: 235° C.; $^1$H-NMR (300 MHz, CDCl$_3$+CD$_3$OD δ TMS) 4.16 (s, 2 H), 7.0–7.3 (m, 7 H), 7.70 (s, 1 H), 7.89 (d, J=8.7 Hz, 2 H).; Anal (C$_{16}$H$_{12}$ClN$_3$O$_2$S.0.25H$_2$O) C, H, N, S.

13(2) 4-[4-Chloro-5-(3,4-dichlorophenyl)imidazol-1-yl]benzenesulfonamide

M. p.: 251° C.; $^1$H-NMR (300 MHz, CDCl$_3$+CD$_3$OD δ TMS): 3.83 (s, 2 H), 6.91 (d, J=8.2 Hz, 1 H), 7.22 (d, J=8.7 Hz, 2 H), 7.33 (m, 1 H), 7.37 (s, 1 H), 7.69 (s,1 H), 7.93 (d, J=8.7 Hz, 2 H); Anal (C$_{15}$H$_{10}$Cl$_3$N$_3$O$_2$S) C, H, N, S.

13(3) 4-[4-Chloro-5-(4-methylphonyl)imidazol-1-yl]benzenesulfonamide

M. p.: 255° C.; $^1$H-NMR (300 MHz, CDCl$_3$+CD$_3$OD δ TMS): 2.29 (s, 3 H), 3.82 (s, 2 H), 7.05 (AB quartet, Δv=0.068, J=8.1 Hz, 4 H), 7.21 (d, J=8.6 Hz, 2 H), 7.64 (s, 1 H), 7.87 (d, J=8.6 Hz, 2 H); Anal (C$_{16}$H$_{14}$ClN$_3$O$_2$S.0.25H$_2$O) C, H, N, S.

13(4) 4-[4-Chloro-5-(4-ethoxyphenyl)imidazol-1-yl]benzenesulfonamide

M. p.: 265° C.; $^1$H-NMR (300 MHz, CDCl$_3$+CD$_3$OD δ TMS): 1.36 (1, J=7.5 Hz, 3 H), 3.99 (q, J=7.5 Hz, 2 H), 4.24 (s, 2 H), 6.81 (d, J=8.5 Hz, 2 H), 7.05 (d, J=8.5 Hz, 2 H), 7.23 (d, J=8.5 Hz, 2 H), 7.67 (s, 1 H), 7.88 (d, J=8.5 Hz, 2 H); Anal (C$_{17}$H$_{16}$ClN$_3$O$_3$S.0.25H$_2$O) C, H, N, S.

13(5) 4-[4-Chloro-5-(3-fluoro-4-methoxyphenyl)imidazol-1-yl]-benzenesulfonamide

M. p.: 211° C.; $^1$H-NMR (300 MHz, CDCl$_3$+CD$_3$OD δ TMS): 3.84 (s, 3 H), 3.85 (s, 2 H), 6.89 (m, 3 H), 7.25 (d, J=8.5 Hz, 2 H), 7.62 (s, 1 H), 7.94 (d, J=8 Hz, 2 H); Anal (Cl$_{16}$H$_{13}$ClFN$_3$O$_3$S) C, H, N, S.

13(6) 4-[4-Chloro-5-(6-chloro-3-pyridyl)imidazol-1-yl]benzenesulfonamide

M. p.: 276–277° C.; $^1$H-NMR (300 MHz, DMS δ TMS): 7.3–8.2 (m, 8 H); Anal (C$_{14}$H$_{10}$Cl$_2$FN$_4$O$_2$S) C, H, N, S.

EXAMPLE 14

4-[5-(4-Fluorophenyl)imidazol-1-yl]benzenesulfonamide

Following a similar procedure to that described in example 1, but using 4-aminobenzenesulfonamide instead of 4-methylsulfonylaniline, the title compound of the example was obtained as a white solid (20% yield).

M. p.: 196–197° C.; $^1$H-NMR (300 MHz, CDCl$_3$+CD$_3$OD δ TMS): 4.0 (s, 2 H+H$_2$O), 7.01 (m, 2 H), 7.11 (m, 2 H), 7.22 (s, 1 H), 7.30 (d, J=8.6 Hz, 2 H), 7.77 (s, 1 H), 7.96 (d, J=8.6 Hz, 2 H); Anal (C$_{15}$H$_{12}$FN$_3$O$_2$S.0.5H$_2$O) C, H, N, S.

EXAMPLE 15

5-(4-Aminophenyl)-4-chloro-1(4-methylsulfonylphenyl)imidazole

A mixture of 1.14 g (3 mmol) of the product obtained in example 4(23), 2.88 g (15 mmol) of SnCl$_2$ and 21 mL of EtOH was refluxed for 1.5 h. The solvent was removed and the residue was basified with 25% NaOH and extracted with CHCl$_3$. The organic phase was dried over MgSO$_4$ and concentrated. The residue was chromatographed on silica gel using hexane-EtOAc mixtures of increasing polarity as eluent. 0.855 g of the product was obtained as a yellow solid (81% yield).

M. p.: 170° C.; $^1$H-NMR (300 MHz, CDCl$_3$+CD$_3$OD δ TMS): 3.08 (s, 3 H), 4.0 (s, 2 H+H$_2$O), 6.60 (d, J=8.5 Hz, 2 H), 6.90 (d, J=8.5 Hz, 2 H), 7.35 (d, J=8.5 Hz, 2 H), 7.66 (s, 1 H), 7.93 (d, J=8.5 Hz, 2 H); Anal (C$_{16}$H$_{14}$ClN$_3$O$_2$S.H$_2$O) C, H, N, S.

EXAMPLE 16

5-6-Ethoxy-3-pyridyl)-1-(4-methylsulfonylphenyl)imidazole

A mixture of 0.20 g (0.6 mmol) of the product obtained in example 1(16), 0.007 g of 18-crown-6, 0.079 g (1.2 mmol) of KOH, 0.1 mL of EtOH and 10 mL of toluene was refluxed in a Dean Stark for 12 h. The mixture was poured on ice and the layers were separated. The aqueous phase was extracted with EtOAc and the organic phases were dried over MgSO$_4$ and concentrated. The residue was chromatographed on silica gel using hexane-EtOAc mixtures of increasing polarity as eluent. 0.20 g of the product was obtained as a yellow solid (100% yield).

M. p.: 167–169° C.; $^1$H-NMR (300 MHz, CDCl$_3$ δ TMS): 1.40 (t, J=7.5 Hz, 3 H), 3.10 (s, 3 H), 4.35 (q, J=7.5 Hz, 2 H), 6.65 (d, J=8.5 Hz, 1 H), 7.30 (m, 2 H), 7.38 (d, J=8.5 Hz, 2 H), 7.79 (m, 1 H), 8.02 (m, 3 H); Anal (C$_{17}$H$_{17}$N$_3$O$_3$S.0.5H$_2$O) C, H, N, S.

EXAMPLE 17

4-Chloro-5(4-dimethylaminophenyl)-1-4-methylsulfonylphenyl)imidazole (17a), 5-(3-chloro-4-dimethylaminophenyl)-1-(4-methylsulfonylphenyl)-imidazole (17b), 4-chloro-(3-chloro-4-dimethylaminophenyl)-1-(4-methyl-sulfonylphenyl)imidazole (17c)

Following a similar procedure to that described in example 4, but starting from the product obtained in example 1(26), the three following compounds were obtained, which were separated by chromatography on silica gel, using hexane-EtOAc mixtures of increasing polarity as eluent.

17a: 10% yield: $^1$H-NMR (300 MHz, CDCl$_3$ δ TMS): 2.85 (s, 6 H), 3.09 (s, 3 H), 6.65 (d, J=8.8 Hz, 2 H), 7.02 (d, J=8.8 Hz, 2 H), 7.35 (d, J=8.6 Hz, 2 H), 7.64 (s, 1 H), 7.95 (d, J=8.6 Hz, 2 H). Anal (C$_{18}$H$_{18}$ClN$_3$O$_2$S) C, H, N, S.

17b: 40% yield: M.p.: 171–172° C.; $^1$H-NMR (300 MHz, CDCl$_3$ δ TMS): 2.82 (s, 6 H), 3.09 (s, 3 H), 6.9 (m, 2 H), 7.2 (m, 2 H), 7.38 (d, J=8.6 Hz, 2 H), 7.73 (s, 1 H), 8.00 (d, J=8.6 Hz, 2 H). Anal (C$_{18}$H$_{18}$ClN$_3$O$_2$S) C, H, N, S.

17c: 10% yield: M.p.: 169° C.; $^1$H-NMR (300 MHz, CDCl$_3$ δ TMS): 2.85 (s, 6 H), 3.09 (s, 3 H), 6.9 (m, 2 H), 7.2 (m, 1 H), 7.35 (d, J=8.6 Hz, 2 H), 7.64 (s, 1 H), 8.00 (d, J=8.6 Hz, 2 H). Anal (C$_{18}$H$_{17}$Cl$_2$N$_3$O$_2$S) C, H, N, S.

EXAMPLE 18

5-(4-Acetylaminophenyl)-4-chloro-(4-methylsulfonylphenyl)imidazole

A mixture of 0.15 g (0.4 mmol) of the product obtained in example 15 and 0.15 mL of Ac$_2$O was refluxed for 4 h. The solvent was removed and the residue was chromatographed on SiO$_2$ using hexane-EtOAc mixtures of increasing polarity as eluent. 0.028 g of the product was obtained as a yellow solid (18% yield).

M. p.: 238–241° C.; $^1$H-NMR (300 MHz, CDCl$_3$ δ TMS): 2.31 (s, 3 H), 3.11 (s, 3 H), 5.32 (s, 1 H), 7.14 (d, J=8.5 Hz, 2 H), 7.32 (d, J=8.5 Hz, 2 H), 7.37 (d, J=8.5 Hz, 2 H), 7.70 (s, 1 H), 8.02 (d, J=8.5 Hz, 2 H); Anal (C$_{18}$H$_{16}$ClN$_3$O$_3$S.0.5H$_2$O) C, H, N, S.

EXAMPLE 19

5-(4-Ethylsulfinylphenyl)-1-(4-methylsulfonylphenyl)imidazole

Following a similar procedure to that described in reference example 1, but starting from the product obtained in example 1(25) and using 1 equivalent of m-chloroperbenzoic acid, the title compound of the example was obtained as a yellow solid (80% yield).

$^1$H-NMR (300 MHz, CDCl$_3$ δ TMS): 1.25 (t, J=7.5 Hz, 3 H), 2.85 (m, 2 H), 3;12 (s, 3 H), 7.26 (d, J=8.5 Hz, 2 H), 7.38 (d, J=8.5 Hz, 2 H), 7.56 (d, J=8.5 Hz, 2 H), 7.80 (s, 1 H), 8.00 (d, J=8.5 Hz, 2 H).

EXAMPLE 20

5-(4-Ethylsulfonylphenyl)-1-(4-methylsulfonylphenyl)imidazole

Following a similar procedure to that described in reference example 1, but starting from the product obtained in example 1 (25), the title compound of the example was obtained as a yellow solid (79% yield).

$^1$H-NMR (300 MHz, CDCl$_3$ δ TMS): 1.30 (t, J=7.5 Hz, 3 H), 3.15 (m, 5 H), 7.26 (d, J=8.5 Hz, 2 H), 7.35 (m, 4 H), 7.84 (m, 3 H), 8.04 (d, J=8.5 Hz, 2 H).

What is claimed is:
1. A compound of formula I:

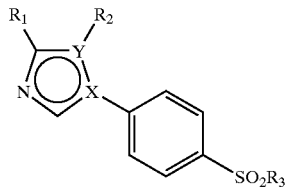

wherein:
one of X or Y represents N and the other represents C;
R$_1$ represents hydrogen, methyl, halogen, cyano, nitro, —CHO, —COCH$_3$ or —COOR$_4$;
R$_2$ represents aryl unsubstituted or substituted with one or more groups independently selected from halogen, C$_{1-8}$ alkyl, C$_{1-8}$ haloalkyl, R$_4$OC$_{0-8}$ alkyl, R$_4$SC$_{0-8}$ alkyl, cyano, nitro, —NR$_4$R$_6$, —NR$_4$SO$_2$R$_5$, —SOR$_5$, —SO$_2$R$_5$, —SO$_2$NR$_4$R$_6$, or —CONR$_4$R$_6$;
R$_3$ represents C$_{1-8}$ alkyl, C$_{1-8}$ haloalkyl or —NR$_4$R$_6$;
R$_4$ represents hydrogen, C$_{1-8}$ alkyl, or arylC$_{0-8}$ alkyl (where the aryl group can be unsubstituted or substituted with one or more groups selected from C$_{1-8}$ alkyl, halogen, C$_{1-8}$ haloalkyl, cyano, nitro, R$_7$OC$_{1-8}$ alkyl, R$_7$SC$_{0-8}$ alkyl, —NR$_7$R$_8$, —NR$_7$COR$_5$, —COR$_7$ or —COOR$_7$);
R$_5$ represents C$_{1-8}$ alkyl or C$_{1-8}$ haloalkyl;
R$_6$ represents hydrogen, C$_{1-8}$ alkyl, arylC$_{1-8}$ alkyl (where the aryl group can be unsubstituted or substituted with one or more groups selected from C$_{1-8}$ alkyl, halogen, C$_{1-8}$ haloalkyl, cyano, nitro, R$_7$OC$_{0-8}$ alkyl, R$_7$SC$_{0-8}$ alkyl, —NR$_7$R$_8$, —NR$_7$COR$_5$, —COR$_7$ or —COOR$_7$), —COR$_8$ or —COOR$_8$;

R$_7$ represents hydrogen, C$_{1-8}$ alkyl or benzyl;

R$_8$ represents C$_{1-8}$ alkyl or C$_{1-8}$ haloalkyl;

aryl in the above definitions represents phenyl or naphthyl;

or a salt, solvate or prodrug thereof.

2. A compound according to claim 1 wherein R$_1$ represents halogen.

3. A compound according to claim 2 wheren R$_1$ represents chloro.

4. A compound according to claim 1 wherein R$_2$ represents phenyl unsubstituted or substituted with one or more groups independently selected from halogen, C$_{1-8}$ alkyl, C$_{1-8}$ haloalkyl, R$_4$OC$_{0-8}$ alkyl, R$_4$SC$_{0-8}$ alkyl, cyano, nitro, —NR$_4$R$_6$, —NR$_4$SO$_2$R$_5$, —SOR$_5$, —SO$_2$R$_5$, —SO$_2$NR$_4$R$_6$, or —CONR$_4$R$_6$.

5. A compound according to claim 1 wherein R$_3$ represents methyl or —NH$_2$.

6. A compound according to claim 1 wherein X represents N.

7. A compound according to claim 5 wherein R$_1$ represents halogen.

8. A compound according to claim 5 wherein R$_1$ represents chloro.

9. A compound according to claim 7 or 8 wherein X represents N.

10. A compound according to claim 9 wherein R$_2$ represents phenyl unsubstituted or substituted with one or more groups independently selected from halogen, C$_{1-8}$ alkyl, C$_{1-8}$ haloalkyl, R$_4$OC$_{0-8}$ alkyl, R$_4$SC$_{0-8}$ alkyl, cyano, nitro, —NR$_4$R$_6$, —NR$_4$SO$_2$R$_5$, —SOR$_5$, —SO$_2$R$_5$, —SO$_2$NR$_4$R$_6$, or —CONR$_4$R$_6$.

11. A compound according to claim 1 selected from:
5-(4-fluorophenyl)-1-(4-methylsulfonylphenyl)imidazole;
5-(4-methylphenyl)-1-(4-methylsulfonylphenyl)imidazole;
5-(2,4-difluorophenyl)-1-(4-methylsulfonylphenyl)imidazole;
1-(4-methylsulfonylphenyl)-5-phenylimidazole;
5-(3,4-dichlorophenyl)-1-(4-methylsulfonylphenyl)imidazole;
5-(4-methoxyphenyl)-1-(4-methylsulfonylphenyl)imidazole;
5-(3-fluoro-4-methoxyphenyl)-1-(4-methylsulfonylphenyl)imidazole;
5-(3-fluorophenyl)-1-(4-methylsulfonylphenyl)imidazole;
5-(3-fluoro-4-methylphenyl)-1-(4-methylsulfonylphenyl)imidazole;
5-(2-fluorophenyl)-1-(4-methylsulfonylphenyl)imidazole;
1-(4-methylsulfonylphenyl)-5-(4-trifluoromethoxyphenyl)imidazole;
5-(2-fluoro-4-methoxyphenyl)-1-(4-methylsulfonylphenyl)imidazole;
5-(3-chloro-4-methylphenyl)-1-(4-methylsulfonylphenyl)imidazole;
5-(3-methoxy-4-methylphenyl)-1-(4-methylsulfonylphenyl)imidazole;
5-(4-chlorophenyl)-1-(4-methylsulfonylphenyl)imidazole;
1-(4-methylsulfonylphenyl)-5-(4-propoxyphenyl)imidazole;
5-(3,5-diethoxyphenyl)-1-(4-methylsulfonylphenyl)imidazole;
5-(4-ethoxyphenyl)-1-(4-methylsulfonylphenyl)imidazole;
1-(4-methylsulfonylphenyl)-5-(4-nitrophenyl)imidazole;
5-(4-methylsulfanylphenyl)-1-(4-methylsulfonylphenyl)imidazole;
5-(4-ethylsulfanylphenyl)-1-(4-methylsulfonylphenyl)imidazole;
5-(4-dimethylaminophenyl)-1-(4-methylsulfonylphenyl)imidazole;
1-(4-fluorophenyl)-5-(4-methylsulfonylphenyl)imidazole;
5-(4-fluorophenyl)-4-methyl-1-(4-methylsulfonylphenyl)imidazole;
4-chloro-5-(4-fluorophenyl)-1-(4-methylsulfonylphenyl)imidazole;
4-chloro-5-(4-methylphenyl)-1-(4-methylsulfonylphenyl)imidazole;
4-chloro-5-(2,4-difluorophenyl)-1-(4-methylsulfonylphenyl)imidazole;
4-chloro-1-(4-methylsulfonylphenyl)-5-phenylimidazole;
4-chloro-5-(3,4-dichlorophenyl)-1(4-methylsulfonylphenyl)imidazole;
4-chloro-5-(4-methoxyphenyl)-1-(4-methylsulfonylphenyl)imidazole;
4-chloro-5-(3-fluoro-4-methoxyphenyl)-1(4-methylsulfonylphenyl)imidazole;
4-chloro-5-(3-fluorophenyl)-1-(4-methylsulfonylphenyl)imidazole;
4-chloro-5-(3-fluoro-4-methylphenyl)-1-(4-methylsulfonylphenyl)imidazole;
4-chloro-5-(2-fluorophenyl)-1-(4-methylsulfonylphenyl)imidazole;
4-chloro-1-(4-methylsulfonylphenyl)-5-(4-trifluoromethoxyphenyl)imidazole;
4-chloro-5-(2-fluoro-4-methoxyphenyl)-1-(4-methylsulfonylphenyl)imidazole;
4-chloro-5-(3-chloro-4-methylphenyl) -1(4-methylsulfonylphenyl)imidazole;
4-chloro-5-(3-methoxy-4-methylphenyl)-1-(4-methylsulfonylphenyl)imidazole;
4-chloro-5-(4-chlorophenyl)-1-(4-methylsulfonylphenyl)imidazole;
4-chloro-1-(4-methylsulfonylphenyl)-5-(4-propoxyphenyl)imidazole;
4-chloro-5-(3,5-diethoxyphenyl)-1-(4-methylsulfonylphenyl)imidazole;
4-chloro-5-(4-ethoxyphenyl)-1-(4-methylsulfonylphenyl)imidazole;
4-chloro-1-(4-methylsulfonylphenyl)-5-(4-nitrophenyl)imidazole;
4-chloro-5-(4-methylsulfanylphenyl)-1-(4-methylsulfonylphenyl)imidazole;
4-chloro-5-(4-ethylsulfanylphenyl)-1-(4-methylsulfonylphenyl)imidazole;
4-bromo-5-(4-fluorophenyl)-1-(4-methylsulfonylphenyl)imidazole;
1-(4-fluorophenyl)-2-methyl-5-(4-methylsulfonylphenyl)imidazole;
2-chloro-1-(4-fluorophenyl)-5-(4-methylsulfonylphenyl)imidazole;
1-(4-fluorophenyl)-5-(4-methylsulfonylphenyl)imidazol-2-carboxaldehyde;
methyl 1-(4-fluorophenyl)-5-(4-methylsulfonylphenyl)imidazol-2-carboxylate;
2-bromo-1-(4-fluorophenyl)-5-(4-methylsulfonylphenyl)imidazole;
1-(4-fluorophenyl)-5-(4-methylsulfonylphenyl)imidazol-2-carbonitrile;
2-chloro-5-(4-methylsulfonlyphenyl)-1-phenylimidazole;
2-chloro-1-(4-methylphenyl)-5-(4-methylsulfonylphenyl)imidazole;
4-[4-chloro-5-(4-fluorophenyl)imidazol-1-yl]benzenesulfonamide;

4-(4-chloro-5-phenylimidazol-1-yl)benzenesulfonamide;
4-[4-chloro-5-(3,4-dichlorophenyl)imidazol-1-yl]
benzenesulfonamide;
4-[4-chloro-5-(4-methylphenyl)imidazol-1-yl]
benzenesulfonamide;
4-[4-chloro-5-(4-ethoxyphenyl)imidazol-1-yl]
benzenesulfonamide;
4-[4-chloro-5-(3-fluoro-4-methoxyphenyl)imidazol-1-yl]
benzenesulfonamide;
4-[5-(4-fluorophenyl)imidazol-1-yl]benzenesulfonamide;
5-(4-aminophenyl)-4-chloro-1-(4-methylsulfonylphenyl)
imidazole;
4-chloro-5-(4-dimethylaminophenyl)-1-(4-methylsulfonylphenyl)imidazole;
5-(3-chloro-4-dimethylaminophenyl)-1-(4-methylsulfonylphenyl)imidazole;
4-chloro-5-(3-chloro-4-dimethylaminophenyl)-1-(4-methylsulfonylphenyl)imidazole;
5-(4-acetylaminophenyl)-4-chloro-1-(4-methylsulfonylphenyl)imidazole;
5-(4-ethylsulfinylphenyl)-1-(4-methylsulfonylphenyl)
imidazole;
5-(4-ethylsulfonylphenyl)-1-(4-methylsulfonylphenyl)
imidazole;
a salt thereof;
a solvate thereof; and
a prodrug thereof.

12. A process for preparing a compound of formula I according to claim 1 which comprises:
(a) when in a compound of formula I $R_1$ represents hydrogen or methyl, reacting an imine of formula II

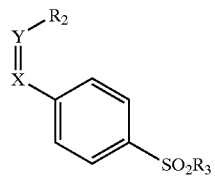

II wherein X, Y, $R_2$ and $R_3$ are as defined in claim 1, with an isocyanide of formula III

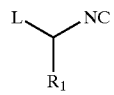

III wherein $R_1$ represents hydrogen or methyl and L represents a leaving group; or (b) when in a compound of formula I $R_3$ represents $C_{1-8}$ alkyl or $C_{1-8}$ haloalkyl, oxidizing a thioether of formula VIII,

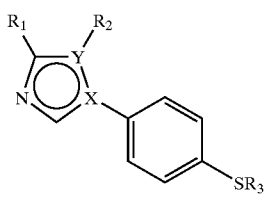

VIII wherein $R_3$ represents $C_{1-8}$ alkyl or $C_{1-8}$ haloalkyl and X, Y, $R_1$ and $R_2$ are as defined in claim 1, with an oxidizing agent; or (c) when in a compound of formula I $R_3$ represents —$NH_2$, reacting a compound of formula IX

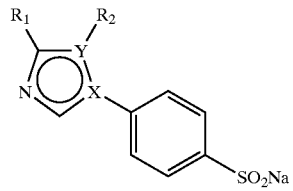

IX wherein X, Y, $R_1$ and $R_2$ are as defined in claim 1, with hydroxylamine-O-sulfonic acid; or (d) when in a compound of formula I $R_3$ represents —$NR_4R_6$, reacting a compound of formula XI

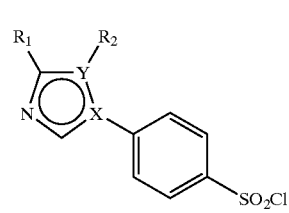

XI wherein X, Y, $R_1$ and $R_2$ are as defined in claim 1, with an amine of formula $HNR_4R_6$; or (e) when in a compound of formula I $R_1$ represents halogen and X represents N, reacting a compound of formula I wherein $R_1$ represents hydrogen with a halogenating agent; or (f) when in a compound of formula I $R_1$ represents halogen and Y represents N, reacting a compound of formula I wherein $R_1$ represents hydrogen with a strong base and a halogenating agent; or (g) converting a compound of formula I into another compound of formula I.

13. A pharmaceutical composition which comprises an effective amount of a compound of formula I according to claim 1 or a pharmaceutically acceptable salt, solvate or prodrug thereof in admixture with one or more pharmaceutically acceptable excipients.

14. A method of treating inflammation, pain or fever in a mammal in need thereof, which comprises administering to said mammal a therapeutically effective amount of a compound of formula I according to claim 1 or a pharmaceutically acceptable salt, solvate or prodrug thereof.

15. A method in accordance with claim 14, wherein said mammal is a human.

16. A method for treating prostanoid-induced smooth muscle contraction in a mammal in need thereof, which comprises administering to said mammal a therapeutically effective amount of a compound of formula I according to claim 1 or a pharmaceutically acceptable salt, solvate or prodrug thereof.

17. A method in accordance with claim 16, wherein said mammal is a human.

18. A method of treating dysmenorrhea, preterm labor, asthma or bronchitis in a mammal in need thereof, which comprises administering to said mammal a therapeutically effective amount of a compound of formula I according to claim 1 or a pharmaceutically acceptable salt, solvate or prodrug thereof.

19. A method in accordance with claim 18, wherein said mammal is a human.

20. A method of treating liver, bladder, pancreas, ovary, prostate, cervix, lung, breast, skin or gastrointestinal cancer in a mammal in need thereof, which comprises administering to said mammal a therapeutically effective amount of a compound of formula I according to claim 1 or a pharmaceutically acceptable salt, solvate or prodrug thereof.

21. A method in accordance with claim 20, wherein said mammal is a human.

22. A method according to claim 20 or 21, wherein said cancer is a gastrointestinal cancer.

23. A method according to claim 22, wherein said cancer is colon cancer.

24. A method of treating cerebral infarction or epilepsy in a mammal in need thereof, which comprises administering to said mammal a therapeutically effective amount of a compound of formula I according to claim 1 or a pharmaceutically acceptable salt, solvate or prodrug thereof.

25. A method according to claim 24, wherein said mammal is a human.

26. A method of treating Alzheimer's disease or dementia in a mammal in need thereof, which comprises administering to said mammal a therapeutically effective amount of a compound of formula I, according to claim 1, or a pharmaceutically acceptable salt, solvate or prodrug thereof.

\* \* \* \* \*